*(12)* United States Patent
Agano et al.

(10) Patent No.: US 9,079,027 B2
(45) Date of Patent: Jul. 14, 2015

(54) RADIATION IRRADIATION DEVICE, RADIATION IRRADIATION METHOD AND PROGRAM STORAGE MEDIUM

(71) Applicant: FUJIFILM Corporation, Tokyo (JP)

(72) Inventors: Toshitaka Agano, Kanagawa (JP); Takao Kuwabara, Kanagawa (JP); Hitoshi Shimizu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/266,220

(22) Filed: Apr. 30, 2014

(65) Prior Publication Data

US 2014/0241508 A1    Aug. 28, 2014

Related U.S. Application Data

(63) Continuation of application No. PCT/JP2012/078244, filed on Oct. 31, 2012.

(30) Foreign Application Priority Data

Nov. 2, 2011  (JP) ................................. 2011-241520
Dec. 28, 2011 (JP) ................................. 2011-289468

(51) Int. Cl.
*A61N 5/10*  (2006.01)
*G21K 1/02*  (2006.01)
(Continued)

(52) U.S. Cl.
CPC ................ *A61N 5/1077* (2013.01); *G21K 1/02* (2013.01); *H01J 35/00* (2013.01); *H01J 35/12* (2013.01); *H01J 35/16* (2013.01); *H05G 2/00* (2013.01); *A61N 2005/1095* (2013.01)

(58) Field of Classification Search
CPC . A61N 5/10; A61N 5/103; A61N 2005/1061; A61N 5/1077; G21K 1/02; G21K 1/04; A61B 6/06; A61B 6/107
USPC .................................... 378/65, 145, 147, 149
See application file for complete search history.

(56) References Cited

U.S. PATENT DOCUMENTS 5,485,500 A      1/1996   Baba et al.
2004/0247073 A1 12/2004   Cho et al.
(Continued)

FOREIGN PATENT DOCUMENTS

JO    2007-267971 A    10/2007
JP      06-76991 A      3/1994
(Continued)

OTHER PUBLICATIONS

International Search Report issued in PCT/JP2012/078244 dated Jan. 29, 2013.

(Continued)

*Primary Examiner* — Jurie Yun
(74) *Attorney, Agent, or Firm* — Birch, Stewart, Kolasch & Birch, LLP

(57) ABSTRACT

A radiation irradiation device is provided that includes: a metal target that emits bremsstrahlung X-rays as a radiation beam due to irradiation with an electron beam; a radiation shielding member that includes a slit-shaped radiation passage portion and that is disposed downstream of the metal target in the radiation beam emission direction and is disposed such that a portion of the radiation beam passes through the radiation passage portion and the radiation beam incident to regions other than the radiation passage portion is blocked; and an electron beam generating device that irradiates, onto the metal target, an electron beam such that a diameter at a generation point of the emitted radiation beam is smaller than a length of an entry portion of the radiation passage portion along a length direction of the entry portion.

21 Claims, 37 Drawing Sheets

(51) Int. Cl.
  *H01J 35/00* (2006.01)
  *H05G 2/00* (2006.01)
  *H01J 35/12* (2006.01)
  *H01J 35/16* (2006.01)

(56) References Cited

U.S. PATENT DOCUMENTS

| 2006/0193441 | A1 | 8/2006 | Cadman |
| 2007/0172022 | A1 | 7/2007 | Schlomka et al. |
| 2009/0316860 | A1 | 12/2009 | Okunuki et al. |
| 2010/0266097 | A1 | 10/2010 | Okunuki et al. |

FOREIGN PATENT DOCUMENTS

| JP | 11-87089 A | 3/1999 |
| JP | 2002-313266 A | 10/2002 |
| JP | 2002-343290 A | 11/2002 |
| JP | 2006-185866 A | 7/2006 |
| JP | 2006-526473 A | 11/2006 |
| JP | 2007-265981 A | 10/2007 |
| JP | 2007-528253 A | 10/2007 |
| JP | 2008-531172 A | 8/2008 |
| JP | 2009-240378 A | 10/2009 |
| JP | 2010-068908 A | 4/2010 |
| JP | 2010-253157 A | 11/2010 |
| JP | 2011-071101 A | 4/2011 |
| JP | 2012-138203 A | 7/2012 |
| WO | WO 2010/032363 A1 | 3/2010 |

OTHER PUBLICATIONS

National Insitute of Radiological Sciences (NIRS) "Basic Research of Microbeam Radiation Therapy", NIRS News No. 134, 2008.

Suzuki et al. "Relationship between cell-killing effect and p53-gene-mediated bystander effect in different human cell lines induced by X-ray microbeams", pp. 40-43, 2010.

Written Opinion of the International Searching Authority issued in PCT/JP2012/078244 dated Jan. 29, 2013.

Office Action, dated May 12, 2015, issued in corresponding Japanese Patent Application No. 2011-241520 with an English translation.

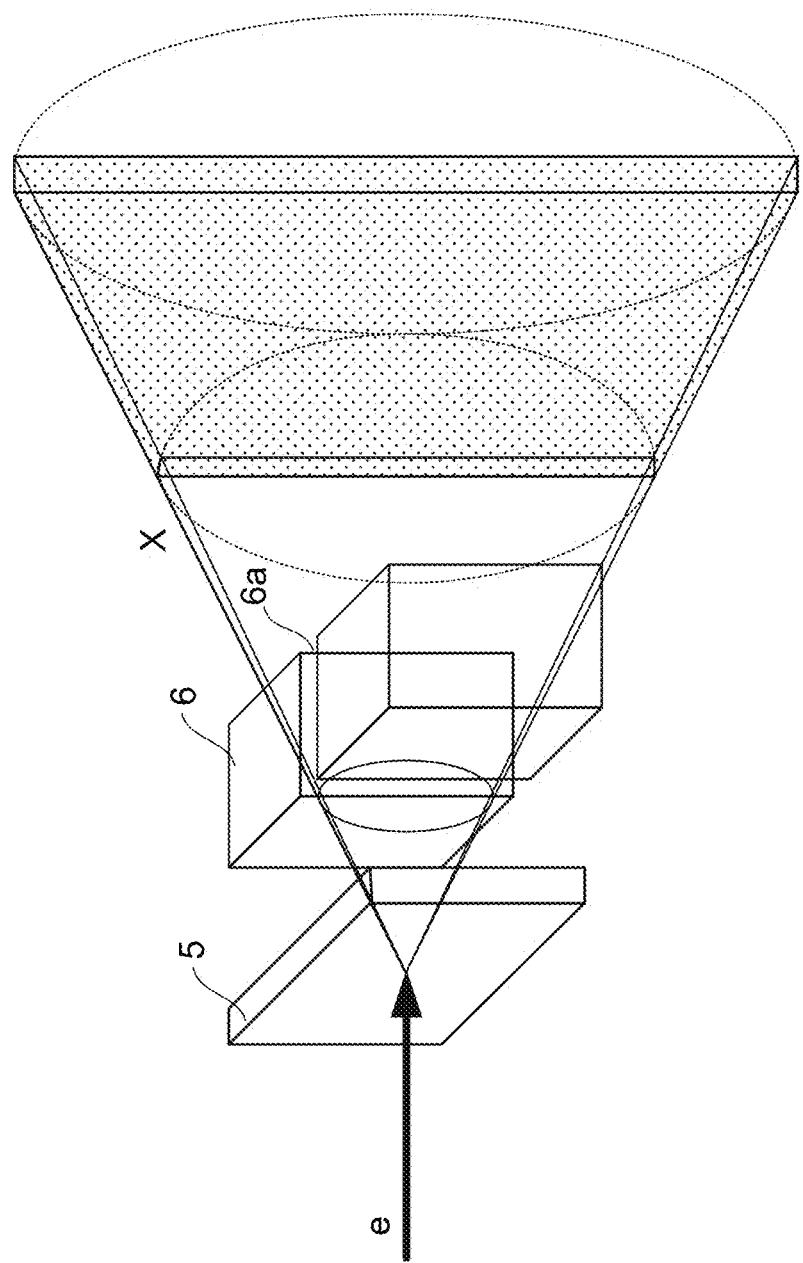

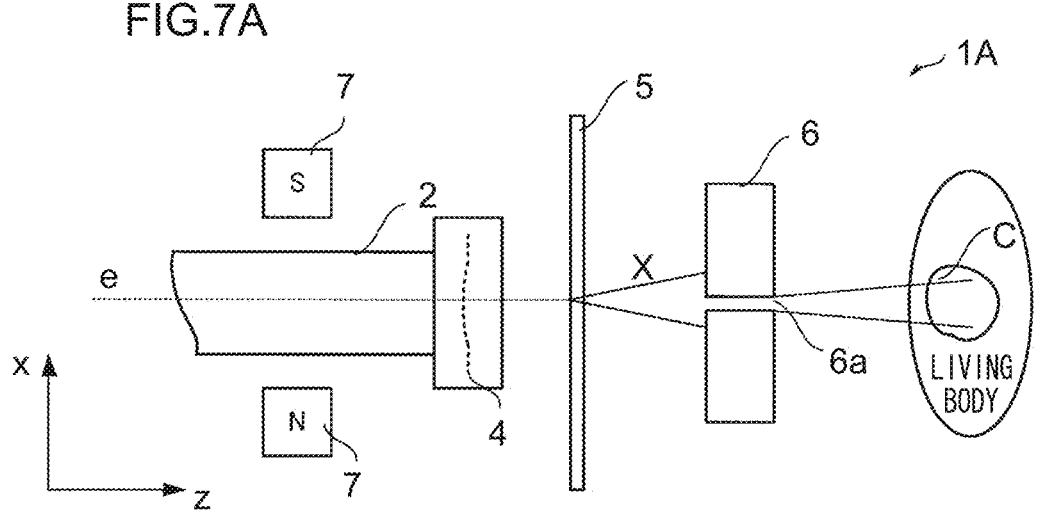
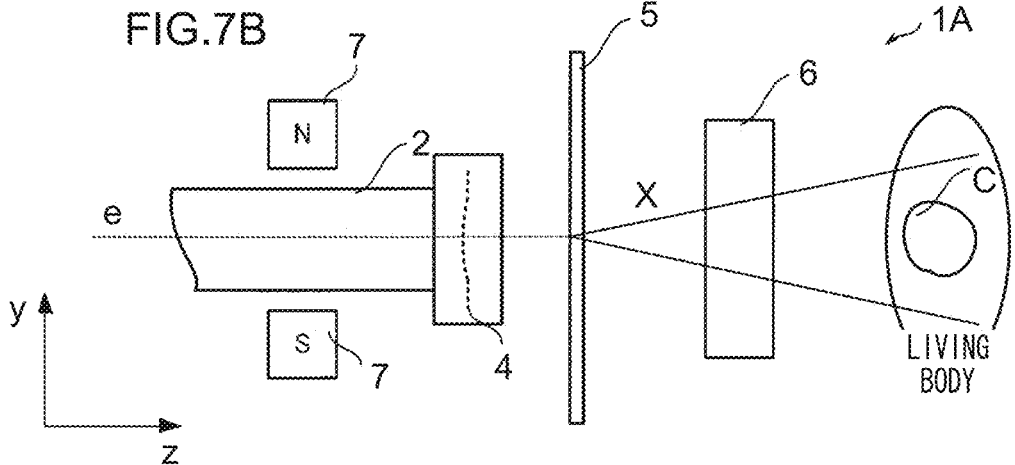

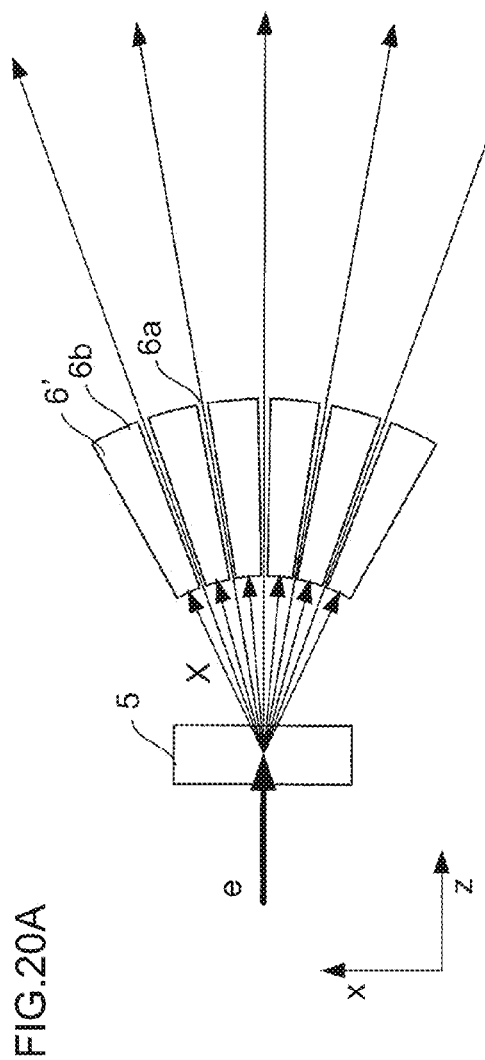
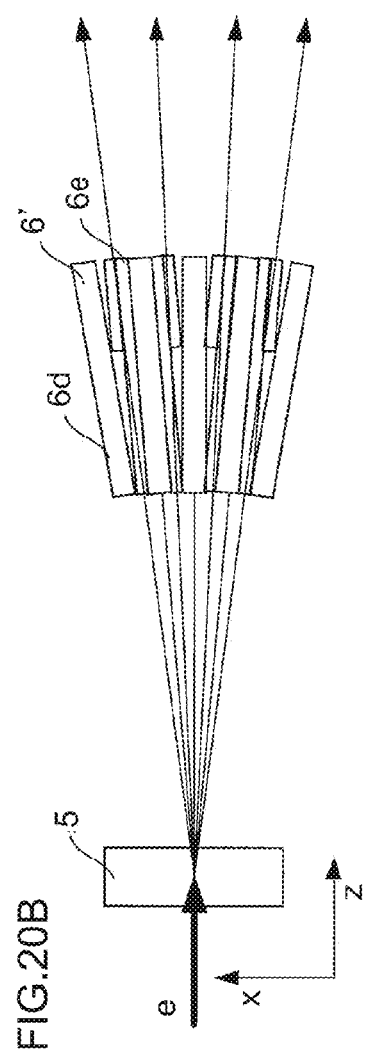

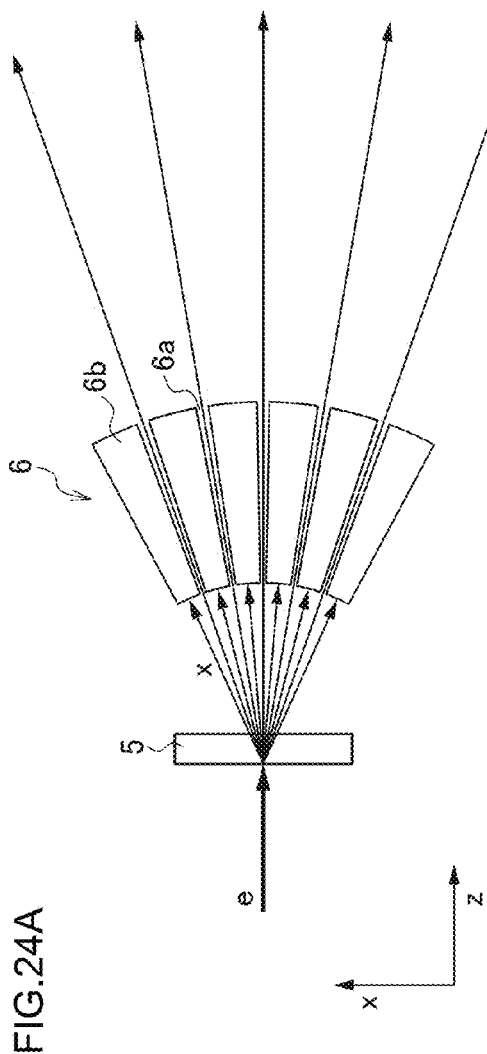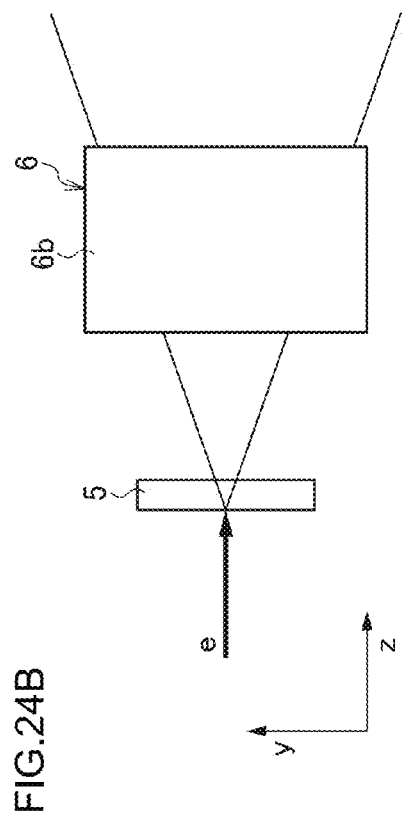
FIG.24A
FIG.24B

RADIATION IRRADIATION DEVICE, RADIATION IRRADIATION METHOD AND PROGRAM STORAGE MEDIUM

CROSS-REFERENCE TO RELATED APPLICATIONS

This application is a continuation application of International Application No. PCT/JP/2012/078244, filed Oct. 31, 2012, the disclosure of which is incorporated herein by reference in its entirety. Further, this application claims priority from Japanese Patent Application No. 2011-241520, filed on Nov. 2, 2011, and Japanese Patent Application No. 2011-289468, filed on Dec. 28, 2011, the disclosures of which are incorporated by reference herein in their entirety.

BACKGROUND OF THE INVENTION

1. Field of the Invention

The present invention relates to a radiation irradiation device that irradiates radiation, a radiation irradiation method of the radiation irradiation device, and a program storage medium.

2. Related Art

As a medical treatment method using radiation, Japanese Patent Application Laid-Open (JP-A) No. 2010-68908 discloses a particle beam treatment device that uses a multileaf collimator, in which the shape of leaf opening portions of the multileaf collimator can be easily and precisely checked. The particle beam treatment device is provided with a first lighting means, a second lighting means and an image capture means at an upstream side of the multileaf collimator with respect to a particle beam irradiation direction. A lighting control means controls switching of the two lighting means based on rotation angle data of the multileaf collimator detected by a rotation angle detection means, thereby enabling suppression of strong diffuse reflection of light by the leaves.

Moreover, recently a treatment method (Microbeam Radiation Therapy: MRT) has been proposed as an oncology treatment, whereby a microbeam obtained by passing a radiation beam through slits with width in the μm is generated, and a tumor is irradiated with the microbeam. In this treatment method excellent therapeutic effects that is capable of destroying only cancer cells without destroying normal cells, have been reported through various experiments.

Technology relating to MRT is introduced in "Relationship between cell-killing effect and p53-gene-mediated bystander effect in different human cell lines induced by X-ray microbeams", [online], 2010, [retrieved Sep. 30, 2011], internet <URL: http://www.spring8.or.jp/pdf/ja/MBTU/H20/14.pdf>, and "Basic Research of Microbeam Radiation Therapy", NIRS News, No. 134, [online], 2008 [retrieved Sep. 30, 2011], internet <URL: http://www.nirs.go.jp/report/nirs_news/200801/hik10p.htm>. These documents describe methods for generating a radiation beam for MRT by utilizing the phenomenon of charged particles such as high energy electrons radiate electromagnetic waves when deflected due to Lorentz force within a magnetic field, and causing synchrotron radiation (a radiation beam) that is the radiated electromagnetic wave to pass through plural linear radiation shielding slits.

Meanwhile, Japanese Patent Application Laid-Open (JP-A) No. H06-76991 describes a method in which a linear accelerator that accelerates an electron beam measures the beam current, beam speed and beam diameter of the electron beam, controls a magnetic field using a solenoid coil according to the measured values, and lowers the emittance of the electron beam.

SUMMARY

In order to implement the technology described in the above documents, a large-scale synchrotron radiation facility is required to generate synchrotron radiation, thereby limiting locations where the technology can be implemented. Patients of cancer, which is the biggest cause of death in Japan, face the inconvenience of having to go to a large-scale synchrotron radiation facility in order to receive MRT using this technology. It is therefore desirable to have MRT devices installed in general hospitals.

However, while radiation shielding slits that are long in depth and narrow in width are employed in order to generate radiation beams for MRT, the slit transmissivity decreases for radiation beams (cone beams) obtained from general radiation sources excluding, for example, parallel radiation beams obtained by synchrotron radiation. As a result, a very large radiation source output is required in order to obtain radiation doses used for treatment, which gives rise to many issues in configuring a device such that heat generation and shielding.

Further, while the MRT technology described in the above documents enables destroying cancer cells while hardly destroying any normal cells as described above, the size of a cross-section profile of the radiation beam that can be generated, in an orthogonal direction to the direction of travel of the radiation beam, is limited. Therefore, the size of a tumor may be wider in range than the cross-section profile in a case of performing MRT radiation treatment, and in such case radiation treatment of the whole tumor cannot be performed.

In consideration of the above circumstances, the present invention provides a radiation irradiation device and a radiation irradiation method capable of generating a radiation beam for MRT without requiring a large-scale facility.

Further, a radiation irradiation device, a radiation irradiation method and a program storage medium are provided, which are capable of irradiating a radiation beam with high therapeutic effect over a wide range, while reducing the destruction of normal cells.

Solution to Problem

A radiation irradiation device according to a first aspect of the present invention includes: a metal target that emits bremsstrahlung X-rays as a radiation beam due to irradiation with an electron beam; a radiation shielding member that includes a slit-shaped radiation passage portion and that is disposed downstream of the metal target in the radiation beam emission direction and is disposed such that a portion of the radiation beam passes through the radiation passage portion and the radiation beam incident to regions other than the radiation passage portion is blocked; and an electron beam generating device that irradiates, onto the metal target, an electron beam such that a diameter at a generation point of the emitted radiation beam is smaller than a length of an entry portion of the radiation passage portion along a length direction of the entry portion.

According to the first aspect, bremsstrahlung X-rays are emitted from the metal target as a radiation beam as a result of being irradiated with the electron beam, and due to the radiation shielding member that includes the slit-shaped radiation passage portion and that is disposed downstream of the metal target in the radiation beam emission direction, a portion of the radiation beam passes through the radiation passage portion and the radiation beam incident to regions other than the radiation passage portion is blocked. In the present aspect, the electron beam having a diameter at the generation point of emission of the radiation beam that is smaller than a length of the entry portion of the radiation passage portion along the length direction of the entry portion is irradiated onto the metal target by the electron beam generating device.

According to the first aspect, the radiation beam is generated by irradiating the electron beam having a diameter at the generation point of emission of the radiation beam that is smaller than the length of the entry portion of the radiation passage portion along the length direction of the entry portion to generate the radiation beam be incident to the slip-shaped radiation passage portion. As a result, this enables generation of a high intensity planar radiation beam, and enables generation of a radiation beam for MRT without requiring a large-scale facility.

In cases in which the shape of the radiation beam is constricted using the above radiation shielding member, it is preferable to make the size of the radiation beam generation point (also referred to below as focal point) extremely as small as possible in order to increase the conversion efficiency of the radiation passage portion.

However, in practice, since it is difficult to increase the conversion efficiency due to reasons such as the use of slit that have an entry portion with small width and is long in the depth direction, there is a need to generate a high brightness radiation beam. In such cases, extremely large heat may be generated at the X-ray focal point of the metal target, and the X-ray focal point portion of the target may be damaged.

Therefore the present aspect may further include a control unit that effects control of forming the electron beam emitted by the electron beam generating device in an elongated shape that is elongated along the length direction of the entry portion of the radiation passage portion, at a stage prior to irradiation onto the metal target. As a result, concentration of electron energy in the metal target may be avoided, and damage to the metal target may be prevented.

The present aspect may include a control unit that effects control of moving an irradiation position of the electron beam emitted from the electron beam generating device onto the metal target along a direction corresponding to the length direction of the entry portion of the radiation passage portion, or a control unit effects control of moving the irradiation position of the electron beam onto the metal target by changing an emission angle of the electron beam emitted from the electron beam generating device.

In the present aspect, the control unit may effect control of changing the electrical charge amount of the electron beam according to a speed of change during the changing of the emission angle of the electron beam. In this way, an electron beam with a uniform electrical charge amount may be generated.

In the present aspect, the metal target may be formed so as to have a minimum thickness such that the metal target is not damaged by the electron beam when irradiated with the electron beam. As a result, the effect due to electron diffusion within the metal target may be reduced, and the conversion efficiency may be improved.

The present aspect may further include a heat transfer member that is thermally coupled to a casing of the electron beam generating device or to an external casing, and is provided so as to contact at least a portion of the metal target. As a result, high temperature increase of the target may be prevented, and damage to the metal target may be prevented.

Moreover, in the present aspect, the heat transfer member may be provided so as to surround a region of the metal target that is irradiated with the radiation beam. This may more effectively prevent damage to the metal target.

In the present aspect, a width of the entry portion of the radiation passage portion may be from 20 μm to 1 mm. As a result, a radiation beam that is appropriate for MRT may be generated.

In the present aspect, a dose of the electron beam may be determined such that a dose of the radiation beam that has passed through the radiation passage portion is from 1 Gy to 1000 Gy, and a dose of the radiation beam that has not been blocked and has passed through a region of the radiation shielding member other than at the radiation passage portion is from $1/1000^{th}$ to $1/10^{th}$ part of the dose of the radiation beam that has passed through the radiation passage portion. As a result, a radiation beam that is appropriate for MRT may be generated.

In the present aspect, the radiation beam emitted from the metal target may be a radiation beam that spreads out in a cone shape; and the radiation shielding member may be provided with plural radiation passage portions at different positions such that the generation point of the radiation beam is positioned on extensions in the depth direction of the radiation passage portions. As a result, X-ray beams appropriate for MRT may be efficiently generated from the radiation beam emitted from the metal target.

In the present aspect, the radiation shielding member may be formed by combining plural plate-shaped shielding members. In this way, the radiation shielding member may be easily manufactured.

In the present aspect, each of the plural radiation passage portions may be formed so as to gradually widen from the entry portion at which the radiation beam is incident toward an exit portion at which the radiation beam is emitted. As a result, the transmissivity of the radiation beam incident to the radiation shielding member at the radiation passing portions may be improved.

The present aspect may further include a first adjustment unit that adjusts the width of the entry portion of each of the plural radiation passage portions. The width of the radiation passing portion entry portions may be thereby adjusted according to the dose of the radiation beam or the like.

The present aspect may further include a second adjustment unit that adjusts mutual positional relationships between the generation point of the radiation beam and the plural radiation passage portions of the radiation shielding member. The mutual positional relationships between the generation point of the radiation beam and the plural radiation passage portions may be thereby adjusted.

In the present aspect, the radiation shielding member may be configured by arraying plural shielding members that are respectively equipped with a face that forms the radiation passage portion between the face and a corresponding face of an adjacent shielding member, such that the generation point of the radiation beam is positioned at extensions in the depth direction of each of the formed radiation passage portions. As a result, the radiation shielding member may be easily manufactured.

The first aspect may further include a control unit that effects control of moving at least one of a first region or a second region, the first region being an irradiation target of the radiation beam and the second region being an irradiation region of the radiation beam that has passed through the radiation shielding member, the moving being performed by relatively moving the second region with respect to the first region such that the radiation beam that has passed through the slit partially overlaps before and after the moving.

In the present configuration, the control unit effects control of moving at least one of the first region or the second region, wherein the first region is an irradiation target of the radiation beam and the second region is an irradiation region of the radiation beam that has passed through the radiation shielding member, and the moving is performed by relatively moving the second region with respect to the first region such that the radiation beam that has passed through the slit partially overlaps before and after the moving.

Namely, radiation beams for MRT are configured by plural planar radiation beams that pass through plural slits. Therefore, in the beam profile of the radiation beams plural peaks (portions corresponding to the slit portions of the radiation shielding member, where the relative radiation intensity is high due to the incident radiation beam passing through plural slits; also referred to below as "peak portions") and valleys (portions corresponding to the portions other than the slits of the radiation shielding member, where the relative radiation intensity is low due to the incident radiation beam being shielded; also referred to below as "valley portions") are formed. It has been found in MRT technical research in recent years that the larger the ratio between the peaks and valleys (hereafter referred to as the PV ratio), the more effective the treatment. Therefore, in the present configuration, control of moving at least one of the first region or the second region is performed, wherein the first region is an irradiation target of the radiation beam and the second region is an irradiation region of the radiation beam that has passed through the radiation shielding member, and the moving is performed by relatively moving the second region with respect to the first region such that the radiation beam that has passed through the slit partially overlaps before and after the moving. Due to this control, the PV ratio is made high even in regions in which plural second regions overlap.

As a result of enabling a high PV ratio in this way even in regions in which plural second regions overlap, radiation beams with high therapeutic effect may be irradiated over a wide range, while reducing damage to normal cells.

Note that in the present configuration, the control unit may effect control during the control of the movement, such that the radiation beam that has passed through the slit partially overlaps before and after the moving in the length direction of the slit. In this way, regions not been irradiated by the radiation beams may be prevented from being generated in the treatment target region and, as a result, the therapeutic effect may be further enhanced.

When moving the position of the second region, in order to achieve a high PV ratio, as described above, it is preferable for the movement to be performed accurately such that the divided regions are continuous with each other, and radiation beams that have passed through respective slits overlap at positions in the length direction of the slits.

However, movement cannot always be performed such that radiation beams that have passed through respective slits overlap at positions in the length direction of the slits, due to factors such as mechanical tolerances or body movement of the patient. In cases in which the positions are misaligned, the peaks become diffused in regions where the second regions overlap, resulting in a lower PV ratio due to the radiation intensity being reduced at peak portions and the radiation intensity being increased at valley portions compared to cases with no misalignment in position.

Thus, in the present configuration, the control unit may effect control during the control of the movement, such that the second region after the moving is rotated about the emission direction of the radiation beam by 90° from before the moving. In this way, a high radiation intensity at the peak portions and a low radiation intensity at the valley portions may be achieved even if some positional misalignment has occurred between adjacent second regions in the slit length direction, and more certain irradiation of a therapy radiation beam of high therapeutic effect may be performed.

In particular, the control unit may effect control of rotating the second region by rotating the radiation shielding member. In this way, easier rotation of the second region may be performed compared to a case in which the irradiated member of the radiation beam is rotated.

Or, the control unit may effect control of moving the second region by moving a support member that supports a target for irradiation by the radiation beam. In this way, easier movement of the second region may be performed compared to a case in which the position of the radiation beam is moved.

The plural slits may be formed in the radiation shielding member such that a focal point of radiation beams is positioned on extensions of the slit faces. As a result, the emitted radiation beam may be utilized more effectively compared to a case in which the focal point of the radiation beam is not positioned on the extensions of the slit faces.

The radiation shielding member may be formed such that the second region is a rectangular shaped region. As a result, regions where the second regions overlap may be made smaller.

The aspect may further include a determination unit that determines whether or not the first region is larger than the second region; and if it is determined by the determination unit that the first region is larger than the second region, the control unit may effect control of the movement such that the first region is divided into plural regions each having a size corresponding to the second region, adjacent regions of the plural regions overlap with each other, and each of the divided regions is taken as the second region. As a result, regions that are not irradiated by the radiation beams may be prevented from being generated, and the therapeutic effect may be further enhanced.

A second aspect of the present invention is a radiation irradiation device including: a radiation emission device that emits a radiation beam; a radiation shielding member that is disposed downstream in an emission direction of the radiation beam with respect to the radiation emission device, that includes plural slits through which the incident radiation beam passes, and that blocks the radiation beam incident elsewhere than the plural slits; and a control unit that effects control of moving at least one of a first region or a second region such that the second region relatively moves with respect to a first region, the first region being an irradiation target of the radiation beam, and the second region being an irradiation region of the radiation beam that has passed through the radiation shielding member, and such that the radiation beam that has passed through the slit partially overlaps before and after the moving.

According to the second aspect, the radiation beam is emitted by the radiation emission device. Due to the radiation shielding member that is disposed downstream of the radiation emission device in the emission direction of the radiation beam, and that includes plural slits through which the incident radiation beam passed, the radiation beam incident to the plural slits passes through, and the radiation beam incident other than at the plural slits is blocked.

In the second aspect a high PV ratio may be achieved even in regions in which the plural second regions overlap and, as a result, radiation beams with high therapeutic effect may be irradiated over a wide range, while reducing damage to normal cells.

A third aspect of the present invention is a radiation irradiation method in a radiation irradiation device including: a metal target that emits bremsstrahlung X-rays as a radiation beam due to irradiation with an electron beam; a radiation shielding member that is disposed downstream of the metal target in the radiation beam emission direction and includes a slit-shaped radiation passage portion having an entry portion with a smaller width than a beam diameter when the radiation beam is incident, a portion of the radiation beam passing through the radiation passage portion and the radiation beam incident to regions other than the radiation passage portion being blocked; and an electron beam generating device that irradiates an electron beam onto the metal target such that, when the electron beam is irradiated onto the metal target, a diameter at a generation point of the emitted radiation beam is smaller than a length of the entry portion of the radiation passage portion along the length direction of the entry portion; the radiation irradiation method including: a control step of controlling a shape of the electron beam emitted from the electron beam generating device so as to be a shape elongated in a direction along the length direction of the entry portion of the radiation passage portion; an emitting step of emitting the radiation beam by irradiating the metal target with the electron beam having a shape controlled by the control step; and a passing step of causing the radiation beam emitted at the emitting step to pass through the radiation passage portion.

According to the present aspect, radiation beams for MRT may be generated without requiring a large-scale facility, and damage to the metal target may also be prevented.

A fourth aspect of the present invention is a radiation irradiation method for a radiation irradiation device including: a metal target that emits bremsstrahlung X-rays as a radiation beam due to irradiation with an electron beam; a radiation shielding member that is disposed downstream of the metal target in the radiation beam emission direction and includes a slit-shaped radiation passage portion having an entry portion with a smaller width than a beam diameter when the radiation beam is incident, a portion of the radiation beam passing through the radiation passage portion and the radiation beam incident to regions other than the radiation passage portion being blocked; and an electron beam generating device that irradiates an electron beam onto the metal target such that, when the electron beam is irradiated onto the metal target, a diameter at a generation point of the emitted radiation beam is smaller than a length of the entry portion of the radiation passage portion along the length direction of the entry portion, the radiation irradiation method including: a control step of controlling an irradiation position on the metal target of the electron beam emitted by the electron beam generating device so as to move in a direction along the length direction of the entry portion of the radiation passage portion; an emitting step of emitting the radiation beam by irradiating the metal target with the electron beam controlled by the control step; and a passing step that causing the radiation beam emitted at the emitting step to pass through the radiation passage portion.

According to the present aspect, radiation beams for MRT may be generated without requiring a large-scale facility, and damage to the metal target may also be prevented.

A fifth aspect of the present invention is a radiation irradiation method including: moving at least one of a first region or a second region such that: at least one of the first region or the second region moves relative to the other, the first region being an irradiation target of a radiation beam emitted from a radiation irradiation device, the second region being an irradiation region of the radiation beam that has passed through a radiation shielding member that is disposed downstream of the radiation irradiation device in a radiation beam emission direction, the radiation shielding member including plural slits through which an incident radiation beam passes and blocking a radiation beam incident elsewhere than the plural slits; and the radiation beam that has passed through the slits partially overlaps before and after the moving.

Since the fifth aspect operates in a similar way to the second aspect, radiation beams with high therapeutic effect may be irradiated over a wide range, while reducing damage to normal cells.

In the movement of the fifth aspect, the radiation shielding member may be rotated about the radiation beam emission direction by 90° with respect to before and after moving the position of the second region. In this way, more certain irradiation of a therapy radiation beam of high therapeutic effect may be performed.

A sixth aspect of the present invention is a non-transitory computer-readable recording medium storing a program that causes a computer to execute radiation irradiation processing, the radiation irradiation processing including: moving at least one of a first region or a second region such that: at least one of the first region or the second region moves relative to the other, the first region being an irradiation target of a radiation beam emitted from a radiation irradiation device, the second region being an irradiation region of the radiation beam that has passed through a radiation shielding member that is disposed downstream of the radiation irradiation device in a radiation beam emission direction, the radiation shielding member including plural slits through which an incident radiation beam passes and blocking a radiation beam incident elsewhere than the plural slits; and the radiation beam that has passed through the slits partially overlaps before and after the moving.

According to the sixth aspect, since a computer is capable of being operated in a similar way to the second aspect, radiation beams with high therapeutic effect may be irradiated over a wide range, while reducing damage to normal cells.

In the movement of the sixth aspect, the radiation shielding member may be rotated about the radiation beam emission direction by 90° with respect to before and after moving the position of the second region. In this way, more certain irradiation of a therapy radiation beam of high therapeutic effect may be performed.

Advantageous Effects of Invention

The aspects described above enable generation of radiation beams for MRT without requiring a large-scale facility.

Moreover, the aspects described above enable irradiation of radiation beams with high therapeutic effect over a wide range, while reducing damage to normal cells.

BRIEF DESCRIPTION OF THE DRAWINGS

FIG. 5 is a perspective view illustrating relevant portions of the radiation irradiation device according to the first exemplary embodiment.

FIG. 7A is a schematic plan view illustrating relevant portions of a radiation irradiation device according to a second exemplary embodiment.

FIG. 7B is a schematic side view illustrating relevant portions of the radiation irradiation device according to the second exemplary embodiment.

FIG. 20A is a schematic plan view illustrating relevant portions of the radiation irradiation device according to the fifth exemplary embodiment.

FIG. 20B is a schematic plan view illustrating a different example of relevant portions of the radiation irradiation device according to the fifth exemplary embodiment.

FIG. 24A is a schematic plan view illustrating a state in which radiation beams generated by an electron beam impacting a target pass through plural slits of a shielding member of the radiation irradiation device according to the sixth exemplary embodiment.

FIG. 24B is a schematic side view illustrating a state in which radiation beams generated by an electron beam impacting a target pass through plural slits of a shielding member of a radiation irradiation device according to an exemplary embodiment.

DETAILED DESCRIPTION

First Exemplary Embodiment

Detailed explanation follows regarding a radiation (X-ray) irradiation device according to a first exemplary embodiment, with reference to the appended drawings.

Figure 1:
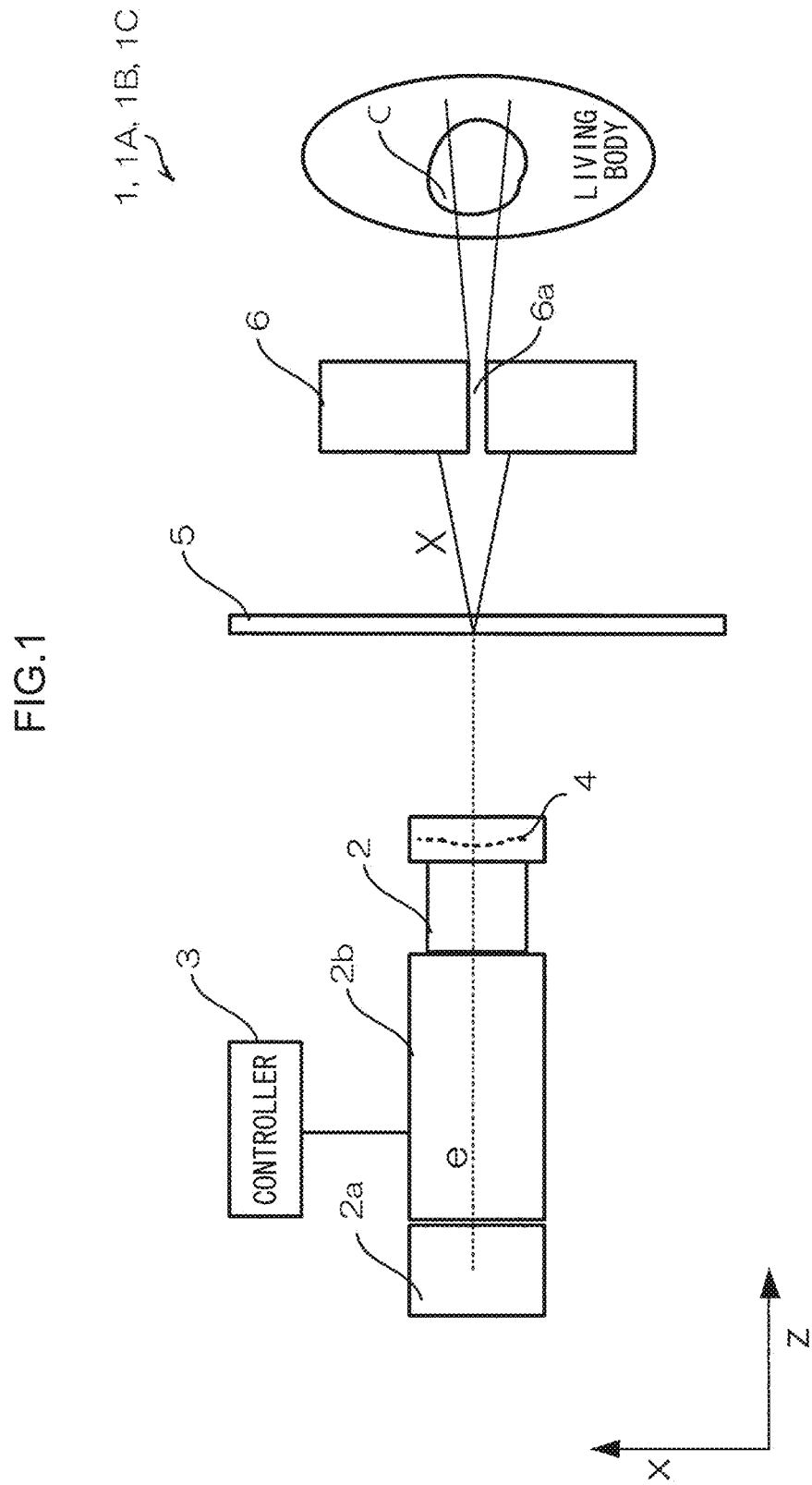
FIG. 1 is a plan view illustrating an overall configuration of a radiation irradiation device according to an exemplary embodiment.

FIG. 1 is a plan view illustrating an overall configuration of a radiation irradiation device 1 according to the first exemplary embodiment.

As illustrated in FIG. 1, the radiation irradiation device 1 includes an electron gun 2a that generates an electron beam e, a low emittance accelerator 2b that accelerates the generated electron beam e while lowering the emittance, and a beam duct 2 that guides the accelerated low emittance electron beam (also referred to below simply as electron beam e) to outside. The radiation irradiation device 1 also includes a controller 3, which performs control of operations such as generation of the electron beam e by the electron gun 2a, measurement of beam current, beam speed and beam diameter of the electron beam e accelerated by the low emittance accelerator 2b, and magnetic field adjustment using a solenoid coil according to these measured values.

The electron beam e that has arrived inside the beam duct 2 is externally emitted through an electron emission window 4. The electron emission window 4 is formed from a thin metal plate, such as of Ti or Be. The inside of the beam duct 2 is maintained in a vacuum, and the electron emission window 4 partitions the inside and the outside of the beam duct 2 so as to prevent, as far as possible, an air ingression into the beam duct 2, which impedes motion of electrons.

A target 5 is provided at the downstream side of the beam duct 2 in the electron beam e emission direction. The target 5 is formed from a heavy metal, such as W or Ta, and generates bremsstrahlung X-rays due to impact of the electron beam e that is irradiated through the electron emission window 4. The generated bremsstrahlung X-rays radiate out as a radiation beam forming a circular conical shape spreading out forward from the point of impact.

The target 5 is formed with the minimum thickness that is not damaged when irradiated with the electron beam e emitted from the beam duct 2. This thereby enables the thickness of the target 5 to be formed as thin as possible while preventing damage to the target 5 by lowering the influence of electron spread within the target 5.

A shielding member 6 is provided at the downstream side of the target 5 in the radiation beam X emission direction. The shielding member 6 has a slit 6a through which a portion of the radiation beam X passes. A width of an entry portion of the slit 6a is formed smaller than the beam diameter of the radiation beam X.

Figure 2:
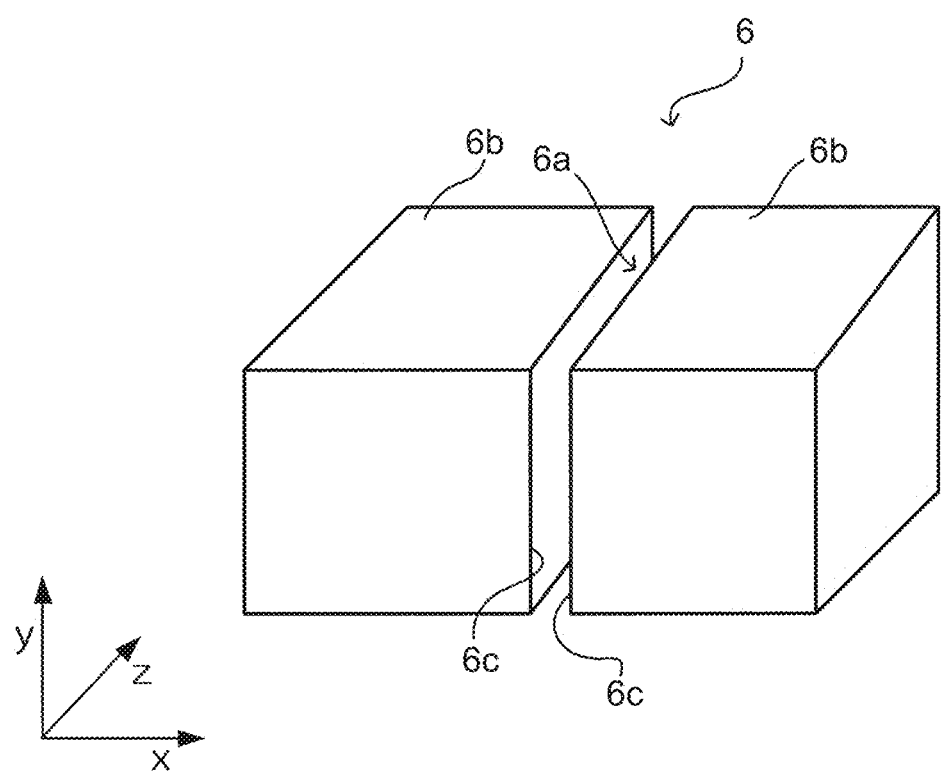
FIG. 2 is a perspective view illustrating a shielding member according to an exemplary embodiment.

FIG. 2 is a perspective view illustrating the shielding member 6 according to the first exemplary embodiment. As illustrated in FIG. 2, the shielding member 6 according to the present exemplary embodiment is configured by a combination of plural (two in the present exemplary embodiment) shielding units 6b of substantially rectangular block shape, each formed from a heavy metal (W in the present exemplary embodiment) having high shielding performance to the radiation beam X.

In the shielding member 6 according to the present exemplary embodiment, the two shielding units 6b are disposed such that one of their faces face each other with a specific gap, which forms the slit 6a through which the radiation beam X passes.

Thus, the radiation irradiation device 1 according to the present exemplary embodiment can be used for MRT by irradiating the shielding member 6 formed with the slit 6a with the radiation beam X, and irradiating a patient with a collimated radiation beam X formed from the irradiated radiation beam X that has passed through the slit 6a.

As a result of extensive research, the inventors have discovered that in cases of performing MRT using radiation beam X, a phenomenon that there is no destruction of tissue and only the nuclei of cells are destroyed occurs if the width of the irradiated radiation beam is set from 20 μm to 1 mm. Therefore, it is preferable to set the width of the slit 6a from 20 μm to 1 mm.

Further, as a result of extensive research, the inventors have discovered that in cases of performing MRT, it is preferable to set the dose of the electron beam e such that the dose of the radiation beam X that has passed through the slit 6a being from 1 Gy to 1000 Gy, and the dose of the radiation beam X that has not been blocked and has passed through regions of the shielding member 6 other than the slit 6a is from $\frac{1}{1000}$ to $\frac{1}{10}$ times the dose of the radiation beam X that has passed through the slit 6a.

Note that the shielding member 6 is not limited to the above configuration, and the shielding member 6 may be configured such that each of the shielding units 6b is formed with one or more plane portions (a plane portion 6c of FIG. 2 in the present exemplary embodiment), and the slit 6a is formed by disposing the plane portions 6c of each of the shielding units 6b so as to face each other in parallel with a gap therebetween. Alternatively, the shielding member 6 may be configured by a single shielding unit 6b provided with a slit that passes through the shielding unit 6b in the depth direction.

Moreover, the slit 6a is not limited to the above gap, and may be formed by a radiotransparent material. In such cases, such a material is disposed between the adjacent shielding units 6b instead of providing a gap.

Figure 3A:
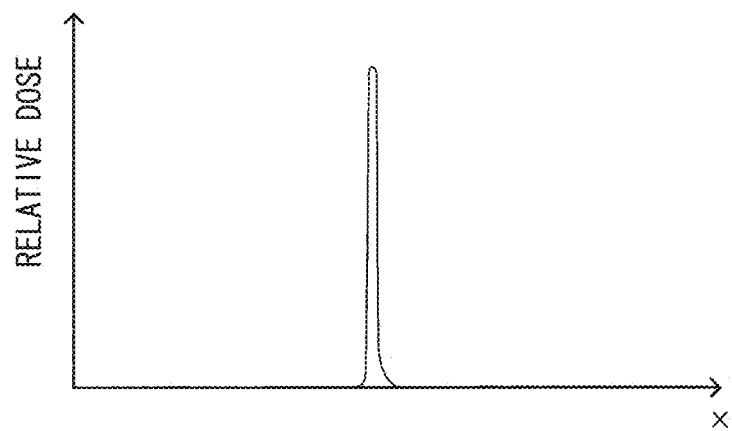
FIG. 3A is a graph illustrating a relationship between the position and relative dose of a radiation beam that has passed through a shielding member of a radiation irradiation device according to a first exemplary embodiment.
Figure 3B:
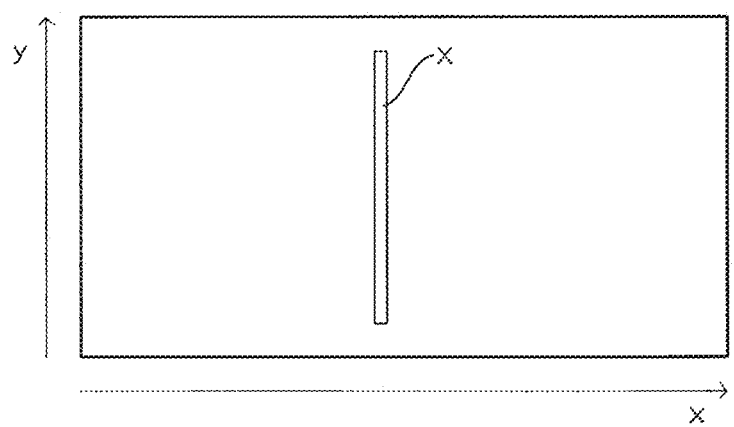
FIG. 3B is a diagram illustrating a shape of a radiation beam that has passed through the shielding member of the radiation irradiation device according to the first exemplary embodiment, as viewed from the emission direction.

FIG. 3A is a graph illustrating the relationship between the position of the radiation beam X that has passed through the shielding member 6 and the relative dose in the radiation irradiation device 1 according to the first exemplary embodiment. FIG. 3b is a diagram that illustrates an example of the shape of the radiation beam X that has passed through the shielding member 6, as viewed from the emission direction in the radiation irradiation device 1 according to the first exemplary embodiment.

As illustrated in FIG. 3A, among the incident radiation beam X, only the X-rays incident to the slit 6a pass through the shielding member 6 and, therefore, a sharp peak is formed in the x direction at the location where the slit 6a is provided. As illustrated in FIG. 3B, a collimated radiation beam X having a shape that substantially matches the profile of the entry portion of the slit 6a is formed.

Explanation next follows regarding the operation of the present exemplary embodiment.

Note that in the radiation irradiation device 1 according to the present exemplary embodiment, explanation follows regarding a case in which a single collimated radiation beam X is generated using the shielding member 6 that has only one slit 6a, and MRT is performed by carrying out irradiation plural times while shifting the position relative to an irradiation target region of a patient.

Figure 4A:
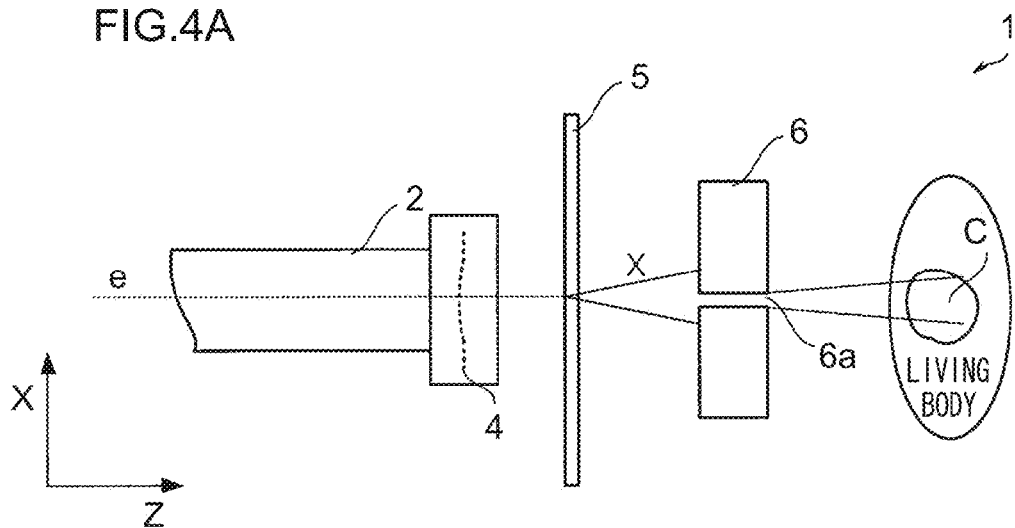
FIG. 4A is a schematic plan view illustrating relevant portions of the radiation irradiation device 1 according to the first exemplary embodiment.
Figure 4B:
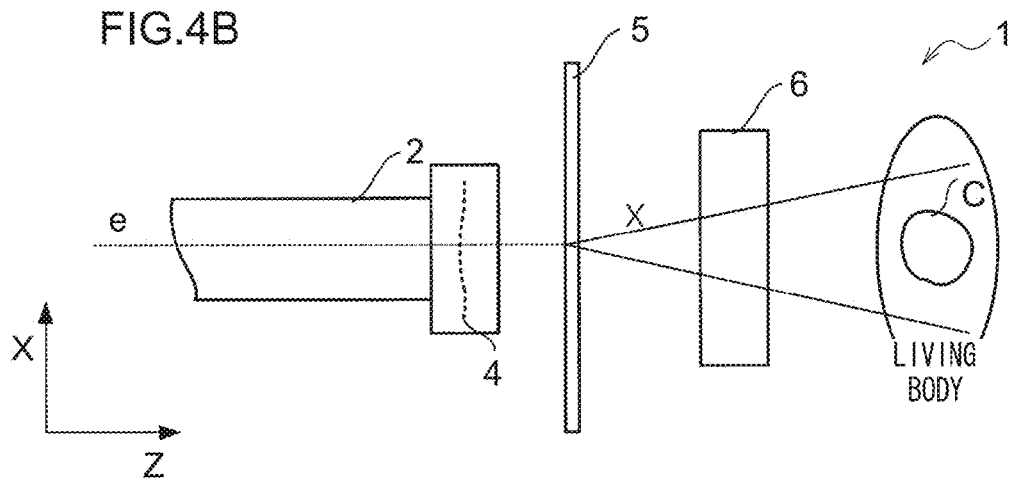
FIG. 4B is a schematic side view illustrating relevant portions of the radiation irradiation device 1 according to the first exemplary embodiment.

FIG. 4A is a schematic plan view illustrating relevant portions of the radiation irradiation device 1 according to the first exemplary embodiment, and FIG. 4B is a schematic side view thereof. As illustrated in FIG. 4A and FIG. 4B, the radiation beam X radiated from the target 5 is incident to the shielding member 6 disposed at the downstream side of the radiation beam X, and after the radiation beam X incident to the shielding member 6 has been constricted in the x direction by the shielding member 6, the collimated radiation beam X obtained thereby is then irradiated onto a tumor C.

Figure 6A:
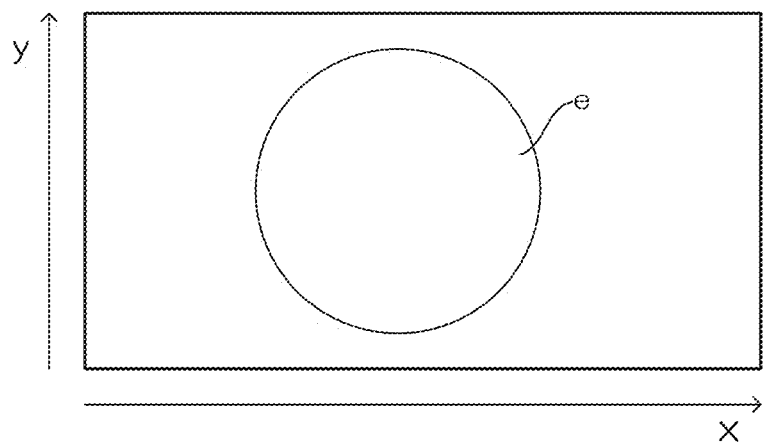
FIG. 6A is a diagram illustrating a shape of a radiation beam immediately before being incident to the shielding member of the radiation irradiation device according to the first exemplary embodiment, as viewed from the emission direction.
Figure 6B:
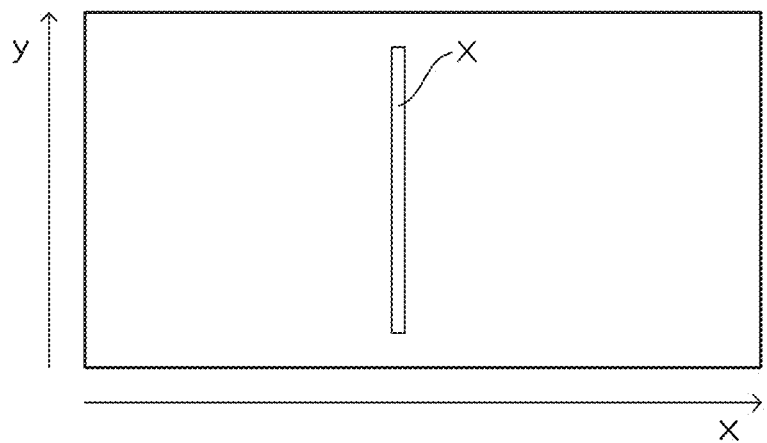
FIG. 6B is a diagram illustrating a shape of a radiation beam immediately after passing through the shielding member of the radiation irradiation device according to the first exemplary embodiment, as viewed from the emission direction.

FIG. 5 is a perspective view illustrating relevant portions of the radiation irradiation device 1 according to the first exemplary embodiment. FIG. 6A is a diagram illustrating the shape of radiation beam X immediately before being incident to the shielding member 6 of the radiation irradiation device 1 according to the first exemplary embodiment, as viewed from the emission direction. FIG. 6B is a diagram illustrating the shape of the radiation beam X immediately after passing through the shielding member 6 of the radiation irradiation device 1 according to the first exemplary embodiment, as viewed from the emission direction.

As illustrated in FIG. 5, the radiated radiation beam X spreads out in a circular conical shape due to impact on the target 5, and as illustrated in FIG. 6A, the shape of the radiation beam X immediately before being incident to the shielding member 6 is thereby a circular shape, as viewed from the emission direction. However, since the radiation beam X irradiated onto the shielding member 6 is constricted into a collimated shape by the shielding member 6, as illustrated in FIG. 6B, the shape of the radiation beam X immediately after being incident to the shielding member 6 is linear as viewed from the emission direction.

Note that although the radiation irradiation device 1 according to the first exemplary embodiment has been explained in a case in which the shielding member 6 with the single slit 6a is used to generate a single collimated radiation beam X, and MRT is performed by carrying out irradiation plural times while shifting the position relative to an irradiation target region on a patient, embodiments are not limited thereto. Configuration may be made such that plural collimated radiation beams are generated by using a shielding member with plural slits, and the radiation beams X are irradiated onto a wide region at a single time.

In cases in which an electron beam accelerator that does not lower the emittance of the electron beam is used, due to the beam diameter of the electron beam becoming larger, the focal point on the target also becomes larger, and the focal point brightness drops for the same charge, which lowers the X-ray dose that passes through the slit.

Therefore, in the radiation irradiation device 1 according to the first exemplary embodiment, the beam diameter of the electron beam e emitted from the electron emission window 4, namely the diameter of the focal point of the corresponding radiation beam X is controlled by the controller 3 so as to be shorter than the length along the length direction (the y direction) of the entry portion of the slit 6a. Further, the focal point of the radiation beam X is preferably controlled so as to be two times or less the width (the length along the short direction, namely, the x direction) of the slit 6a. This enables to prevent a drop in the X-ray dose that passes through the slit by preventing a drop in focal point brightness for the same charge, thereby obtaining an excellent treatment effect by irradiating the radiation beam X onto a patient.

Second Exemplary Embodiment

Detailed explanation follows regarding operation of a radiation irradiation device 1A according to a second exemplary embodiment, with reference to the appended drawings. The radiation irradiation device 1A according to the second exemplary embodiment is configured by providing deflection magnets 7 at the periphery of the beam duct 2 of the radiation irradiation device 1 according to the first exemplary embodiment. Note that the same reference numerals are allocated to the same configurations as those of the first exemplary embodiment, and duplicate explanation thereof is omitted.

FIG. 7A is a schematic plan view illustrating relevant portions of the radiation irradiation device 1A according to the second exemplary embodiment, and FIG. 7B is a schematic side view thereof. As illustrated in FIG. 7A and FIG. 7B, the radiation irradiation device 1A according to the second exemplary embodiment has the deflection magnets 7 provided at the periphery of the beam duct 2.

Figure 8:
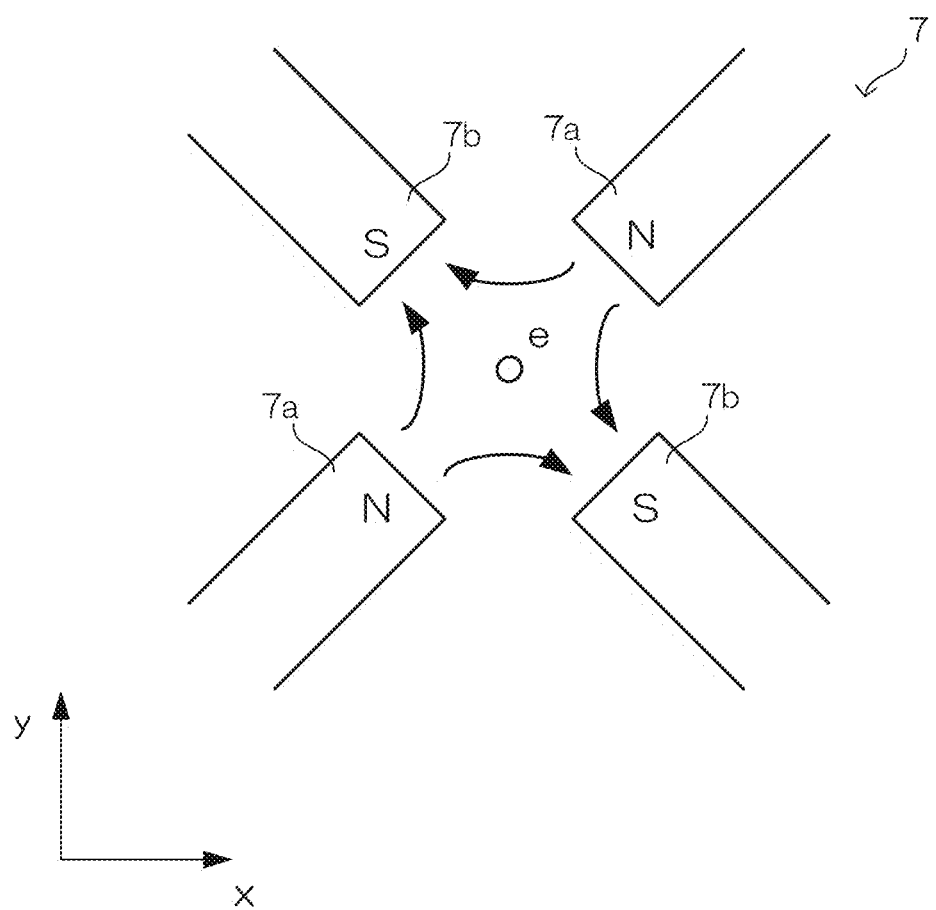
FIG. 8 is a diagram illustrating an example of a layout of deflection magnets in the radiation irradiation device according to the second exemplary embodiment.

FIG. 8 is a diagram illustrating an example of a layout of the deflection magnets 7 in the radiation irradiation device 1A according to the second exemplary embodiment. As illustrated in FIG. 8, the deflection magnets 7 are configured as a quadrupole electromagnet, with two N poles 7a, and two S poles 7b. In a same plane orthogonal to the emission direction of the electron beam e, the N magnets 7a are disposed so as to face each other across the electron beam e along a direction angled at 45° to the x direction, and the S magnets 7b are disposed so as to face each other across the electron beam e along a direction orthogonal to that of the N magnets 7a. Due to the electron beam e being converged in the x direction by the deflection magnets 7, the electron beam e is stretched in the y direction, resulting in a collimated shape elongated in the y direction.

Figure 9:
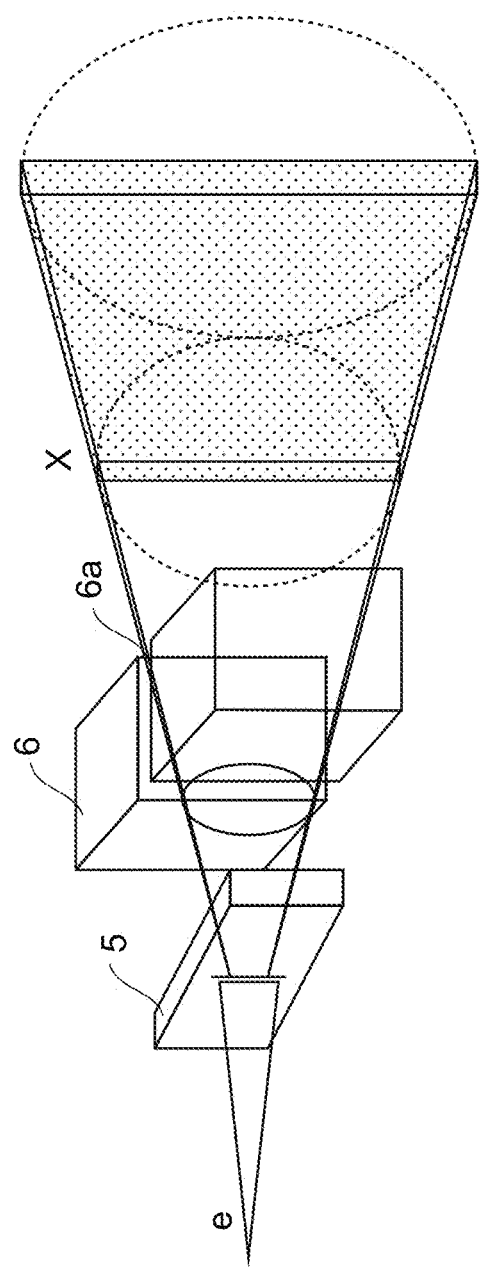
FIG. 9 is a perspective view illustrating relevant portions of the radiation irradiation device according to the second exemplary embodiment.
Figure 10A:
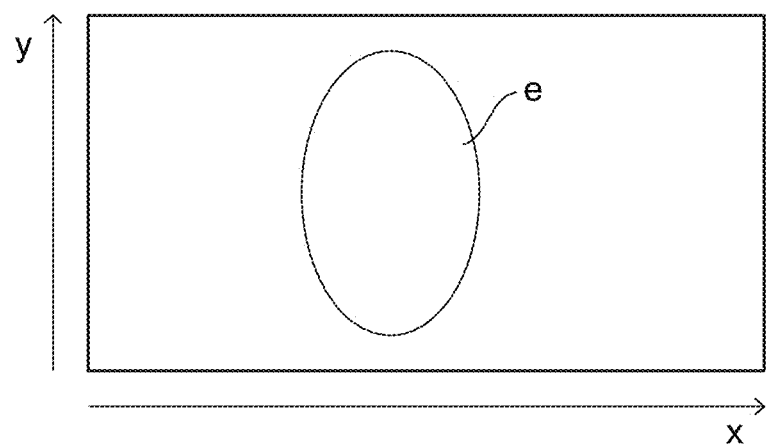
FIG. 10A is a diagram illustrating a shape of a radiation beam immediately before being incident to a shielding member of the radiation irradiation device according to the second exemplary embodiment, as viewed from the emission direction.
Figure 10B:
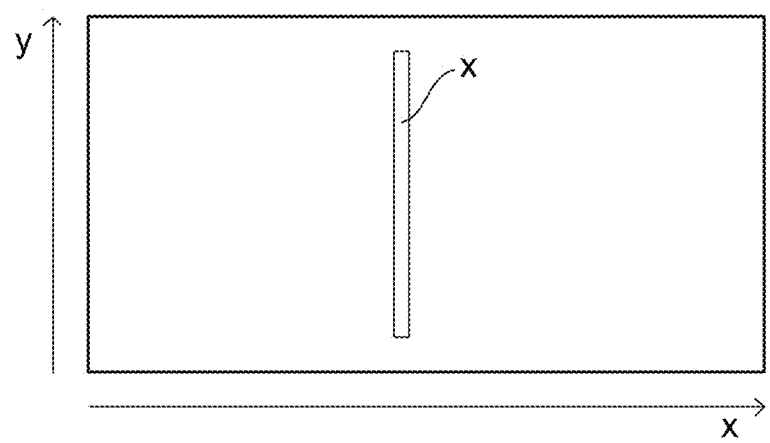
FIG. 10B is a diagram illustrating a shape of a radiation beam immediately after passing through the shielding member of the radiation irradiation device according to the second exemplary embodiment, as viewed from the emission direction.

FIG. 9 is a perspective view illustrating relevant portions of the radiation irradiation device 1A according to the second exemplary embodiment. FIG. 10A is a diagram of the shape of the radiation beam X immediately before being incident to the shielding member 6 of the radiation irradiation device 1A according to the second exemplary embodiment, as viewed from the emission direction. FIG. 10B is a diagram of the shape of the radiation beam X immediately after passing through the shielding member 6 of the radiation irradiation device 1A according to the second exemplary embodiment, as viewed from the emission direction.

As illustrated in FIG. 9, the electron beam e impacts the target 5 in a state elongated in the y direction by the deflection magnets 7, and thus the radiation beam X radiated from the target 5 spreads out in a circular conical shape, such that, as illustrated in FIG. 10A, the shape of the radiation beam X immediately before being incident to the shielding member 6 as viewed from the emission direction is an elliptical shape stretched in the y direction. However, due to the radiation beam X incident to the shielding member 6 being constricted into a collimated shape by the shielding member 6, as illustrated in FIG. 10B, the shape of the radiation beam X immediately after being incident to the shielding member 6 as viewed from the emission direction becomes a collimated shape.

In this way, since the electron beam e that has been adjusted such that the diameter of the focal point of the radiation beam X is shorter than the length of the length direction of the entry portion of the slit 6a, is stretched in the y direction before impacting the target 5 corresponding to the shape of the slit 6a, the concentration of electron energy at the target 5 is reduced, and damage to the target 5 can be prevented.

Moreover, by making the shape of the radiation beam X as viewed from the emission direction approximate to the shape of the entry portion of the slit 6a of the shielding member 6, the radiation beam X that is wastefully discarded by being blocked by the shielding units 6b is reduced and the radiation beam X that passes through the slit 6a is increased, thereby enabling a higher dose of radiation beam X to be irradiated onto the tumor C. Moreover, the amount of electrons in the electron beam e that contribute to generating the radiation beam X passing through the slit 6a is increased by making the focal point of the radiation beam X (corresponding to the beam diameter of the electron beam e) small (in the present exemplary embodiment, the diameter of the electron beam e is shorter than the length in the length direction of the slit 6a). Thereby, a high output radiation beam can be generated without a fall in planar beam conversion efficiency, even while reducing the electron density per unit time.

Note that in the radiation irradiation device 1A according to the second exemplary embodiment, a quadrupole electromagnet is used as the deflection magnets 7. However, embodiments are not limited thereto, and permanent magnets may be used as the deflection magnets 7. In such cases, a configuration similar to that described above can be made by using two N poles and two S poles.

Third Exemplary Embodiment

Detailed explanation follows regarding a radiation irradiation device 1B according to a third exemplary embodiment, with reference to the appended drawings. The radiation irradiation device 1B according to the third exemplary embodiment is configured by providing an alternating current magnet 8 in place of the deflection magnets 7 at the periphery of the beam duct 2 of the radiation irradiation device 1A according to the second exemplary embodiment. The same reference numerals are allocated to the same configurations as those of the first exemplary embodiment and the second exemplary embodiment, and duplicate explanation thereof is omitted.

Figure 11A:
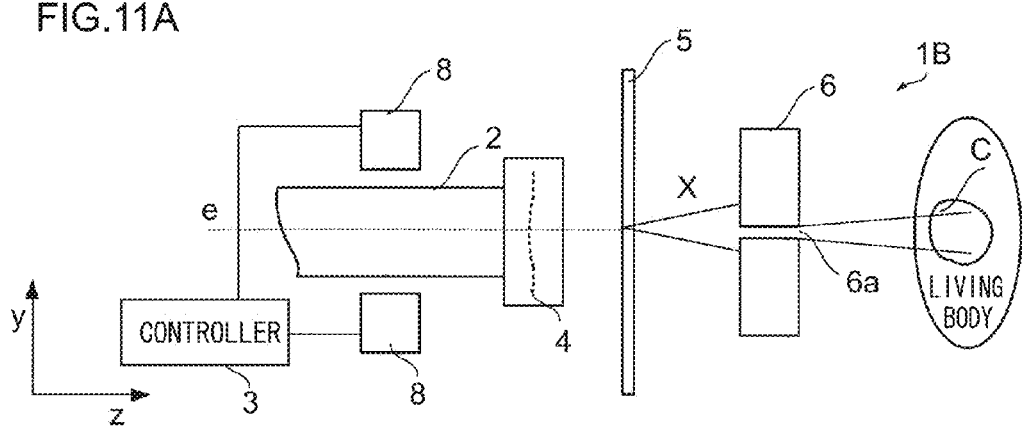
FIG. 11A is a schematic plan view illustrating relevant portions of a radiation irradiation device according to a third exemplary embodiment.
Figure 11B:
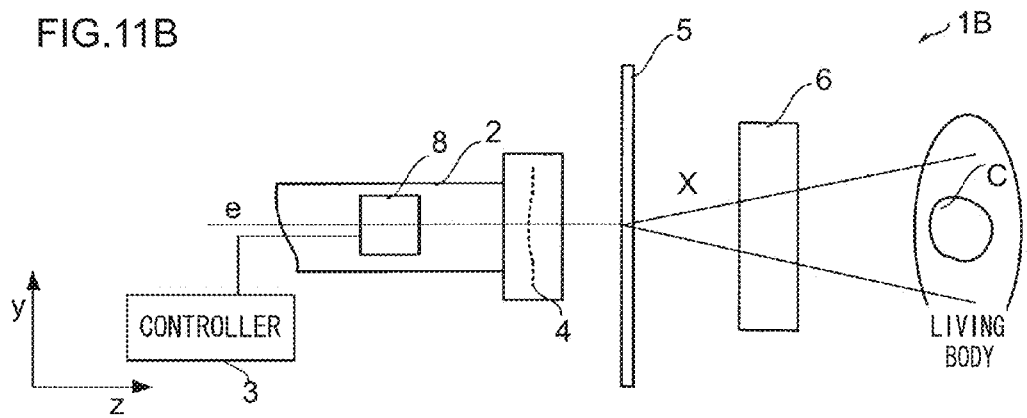
FIG. 11B is a schematic side view illustrating relevant portions of the radiation irradiation device according to the third exemplary embodiment.

FIG. 11A is a schematic plan view illustrating relevant portions of the radiation irradiation device 1B according to a third exemplary embodiment, and FIG. 11B is a schematic side view thereof. As illustrated in FIG. 11A and FIG. 11B, in the radiation irradiation device 1B according to the third exemplary embodiment, the alternating current magnet 8 that is connected to the controller 3 is provided at the periphery of the beam duct 2. The controller 3 includes at least a central processing unit (CPU), read only memory (ROM), and random access memory (RAM).

Figure 12A:
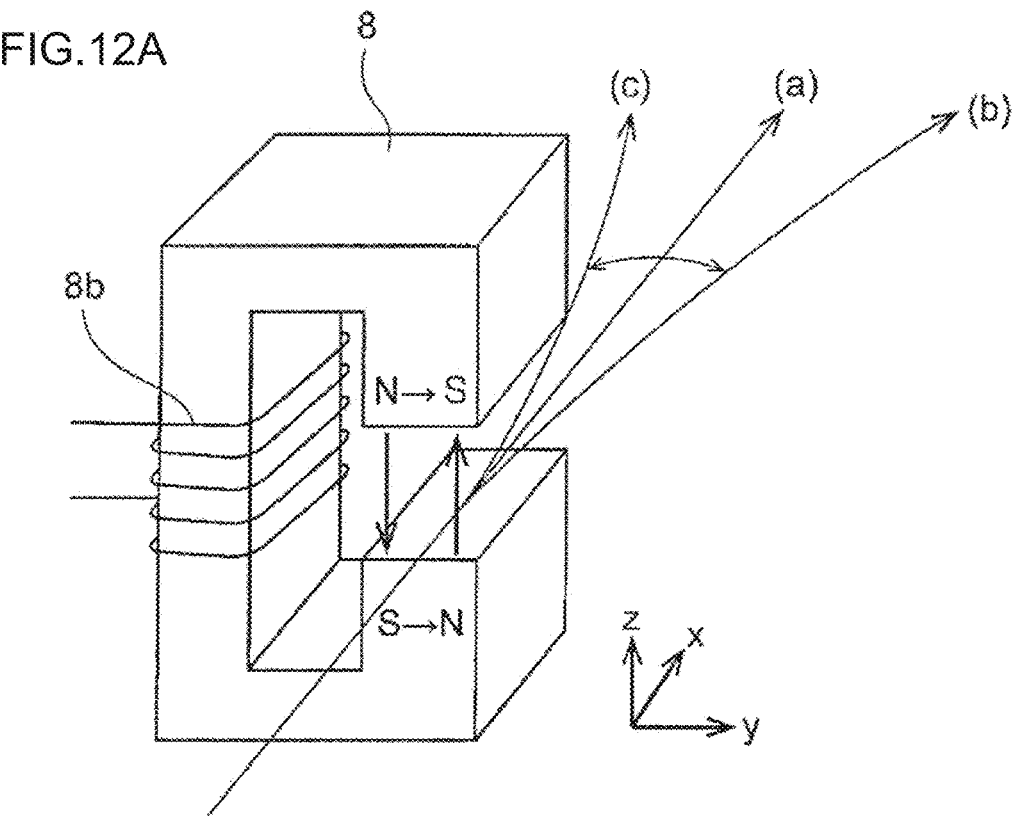
FIG. 12A is a perspective view illustrating a configuration of an alternating current magnet of the radiation irradiation device according to the third exemplary embodiment.
Figure 12B:
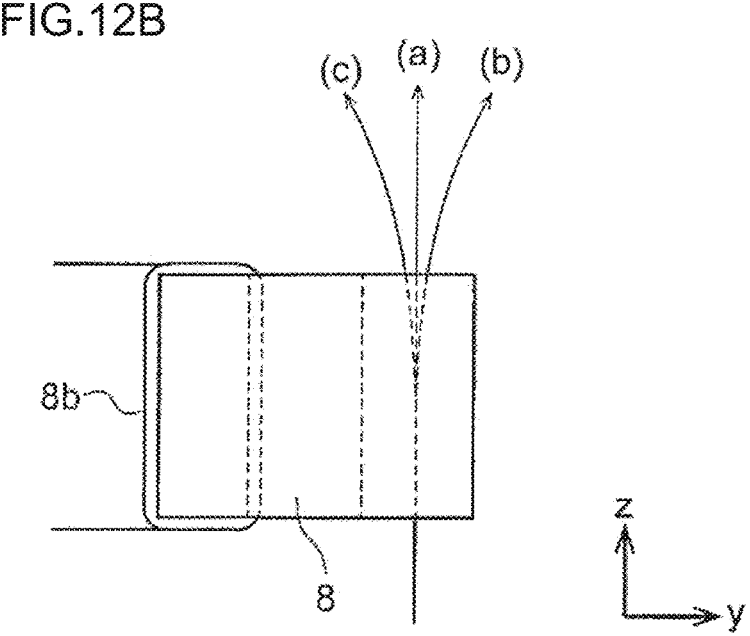
FIG. 12B is a schematic side view illustrating the configuration of the alternating current magnet of the radiation irradiation device according to the third exemplary embodiment.

FIG. 12A is a perspective view illustrating a configuration of the alternating current magnet 8 of the radiation irradiation device 1B according to the third exemplary embodiment, and FIG. 12B is a schematic side view thereof. As illustrated in FIG. 12A and FIG. 12B, the alternating current magnet 8 is magnetized by current flowing in a coil 8b under control of the controller 3, and is polarized such that one end portion to be an N pole and the other end portion to be an S pole.

The alternating current magnet 8 of the radiation irradiation device 1B of the present exemplary embodiment is disposed such that the two end portions face each other across the electron beam e in the y direction, along the same plane orthogonal to the emission direction of the electron beam e. In a state in which current is not flowing in the alternating current magnet 8, as illustrated by (a) in FIG. 12B, the electron beam e travels without deviation along its incident direction. However, in a case in which the controller 3 effects control to make current flow in the coil 8b such that one end portion of the alternating current magnet 8 is an N pole and the other end portion is an S pole, as illustrated by (b) in FIG. 12B, the direction of travel of the electron beam e is deflected according to Fleming's left-hand rule.

Moreover, from this state, in a case in which the controller 3 effects control to change the flow of current in the coil 8b such that the one end portion changes from an N pole to an S pole, and the other end portion changes from an S pole to an N pole, as illustrated by (c) in FIG. 12B, the direction of travel of the electron beam e is deflected according to Fleming's rule towards the opposite side to that of (b) with respect to the incident direction. By changing the polarity of the alternating current magnet 8 in this manner, the emission angle of the electron beam e is changed so as to sweep across the y direction, thereby sweeping the irradiation position of the electron beam e on the target 5 in the y direction.

Figure 13:
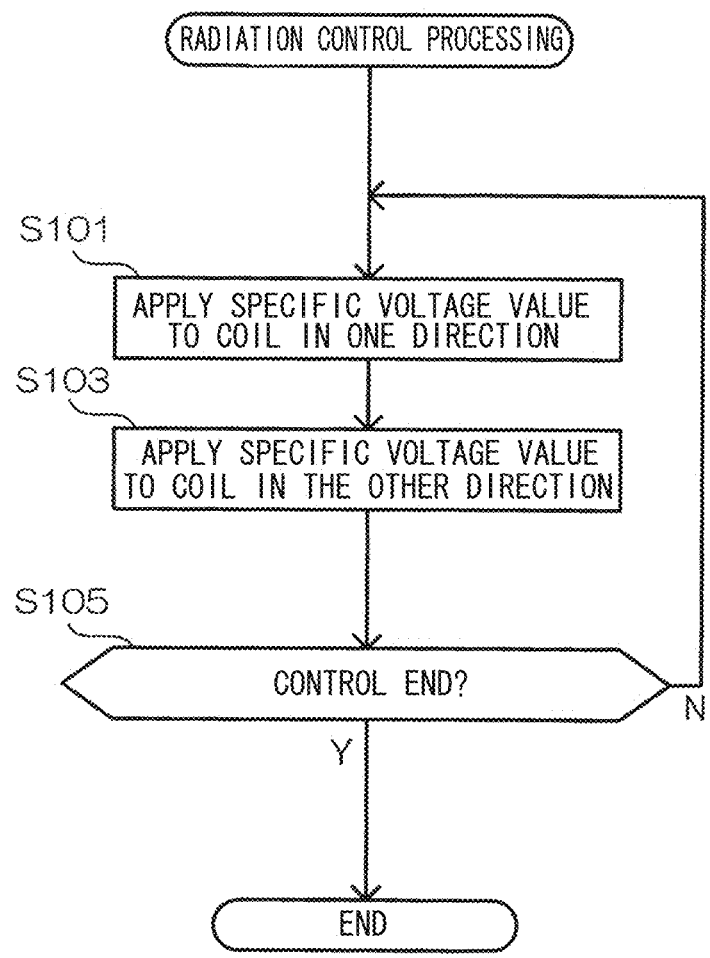
FIG. 13 is a flow chart illustrating a flow of processing of an X-ray control processing program executed by the radiation irradiation device according to the third exemplary embodiment.

Explanation next follows regarding a flow of performing radiation control processing in the radiation irradiation device 1B according to the present exemplary embodiment. FIG. 13 is a flow chart illustrating a flow of processing of a radiation control processing program executed by the CPU of the controller 3 of the alternating current magnet 8 in the radiation irradiation device 1B according to the present exemplary embodiment. The program is pre-stored in a specific region of the ROM, which is a storage medium provided to the controller 3.

At step S101, the controller 3 applies a voltage of a specific voltage value to the coil 8b in one direction. The specific voltage value is a predetermined voltage value, and data indicating the voltage value is stored in the ROM of the controller 3.

At step S103, the controller 3 applies a voltage of a specific voltage value to the coil 8b in the other direction. This specific voltage value is a predetermined voltage value (the same value as the specific voltage value at step S101 in the present exemplary embodiment), and data indicating this voltage value is stored in the ROM of the controller 3.

At step S105, the controller 3 determines whether or not a time of terminating the voltage control has arrived. In the radiation irradiation device 1B of the present exemplary embodiment, the timing for terminating the voltage control is pre-set to a predetermined duration stored in the ROM of the controller 3, as a radiation beam X irradiation duration onto the patient. Note that the timing for terminating the voltage control is not limited to this, and the timing for terminating the voltage control may be identified based on, for example, instruction input by a user.

In this manner, in the radiation irradiation device 1B of the present exemplary embodiment, due to performing the processing from step S101 to step 105, a magnetic field is generated in the alternating current magnet 8, and the electron beam e is swept in the y direction by successively switching over the polarity of the two end portions of the alternating current magnet 8.

Figure 14:
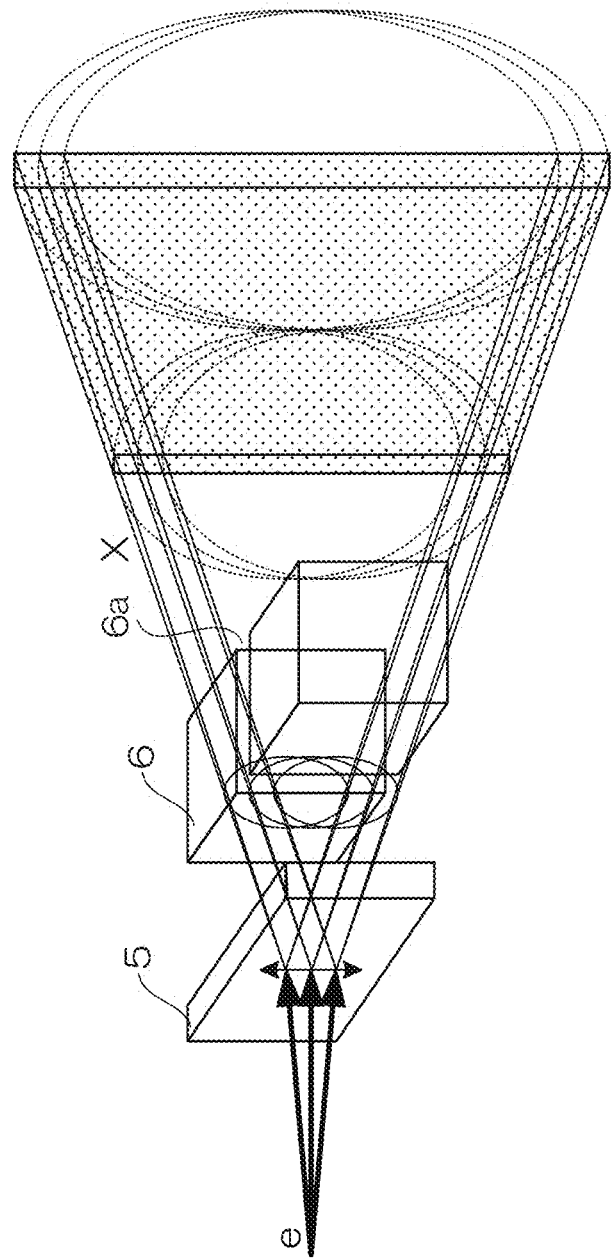
FIG. 14 is a perspective view illustrating relevant portions of the radiation irradiation device according to the third exemplary embodiment.
Figure 15A:
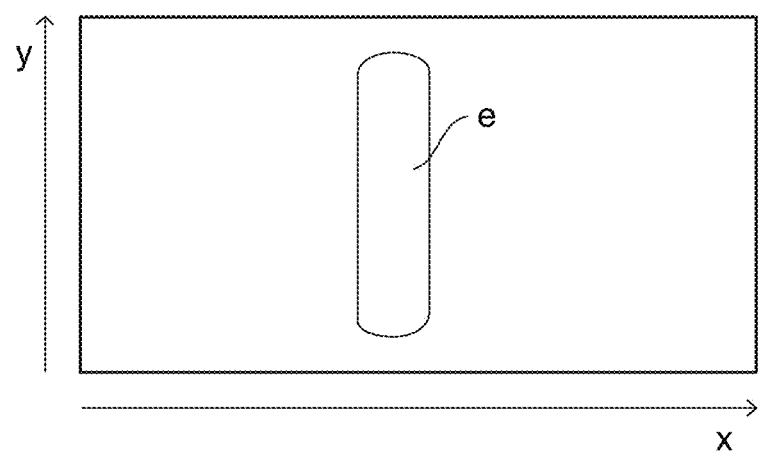
FIG. 15A is a diagram illustrating a shape of a radiation beam immediately before being incident to a shielding member of the radiation irradiation device according to the third exemplary embodiment, as viewed from the emission direction.
Figure 15B:
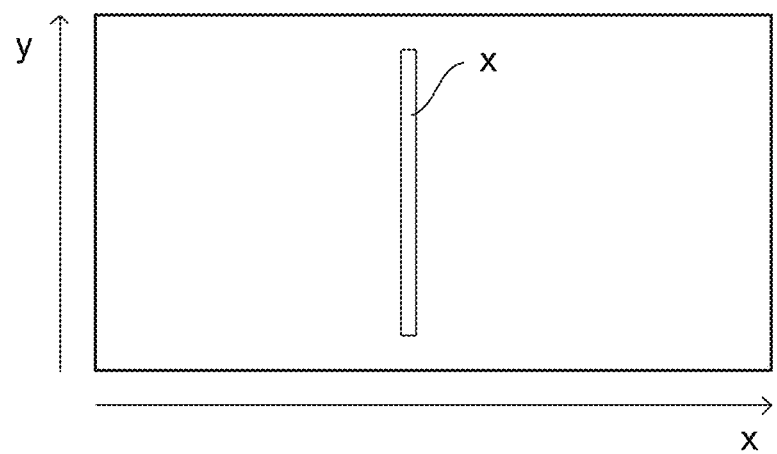
FIG. 15B is a diagram illustrating a shape of a radiation beam immediately after passing through the shielding member of the radiation irradiation device according to the third exemplary embodiment, as viewed from the emission direction.

FIG. 14 is a perspective view illustrating relevant portions of the radiation irradiation device 1B according to the third exemplary embodiment. FIG. 15A is a diagram illustrating a shape of the radiation beam X immediately before being incident to the shielding member 6 in the radiation irradiation device 1B according to the third exemplary embodiment, as viewed from the emission direction. FIG. 15B is a diagram illustrating a shape of the radiation beam X immediately after passing through the shielding member 6 of the radiation irradiation device 1B according to the third exemplary embodiment, as viewed from the emission direction.

As illustrated in FIG. 14, the electron beam e impacts the target 5 while being swept in the y direction due to the alternating current magnet 8. Since the radiation beam X radiated from the target 5 spreads out in a circular conical shape, as illustrated in FIG. 15A, the shape of the radiation beam X immediately before being incident to the shielding member 6 as viewed from the emission direction is a shape formed by a circular shaped profile being swept in the y direction. However, since the radiation beam X incident to the shielding member 6 is constricted into a collimated shape by the shielding member 6, as illustrated in FIG. 15B, the shape of the radiation beam X immediately after being incident to the shielding member 6 is a collimated shape that matches the shape of the entry to the slit 6a.

In this way, since the electron beam e, which has been adjusted such that the diameter of the focal point of the radiation beam X is shorter than the length of the length direction of the entry portion of the slit 6a, sweeps in the y direction to match the shape of the slit 6a before impacting the target 5, the concentration of electron energy at the target 5 is reduced, and damage to the target 5 may be prevented.

Further, similarly to in the second exemplary embodiment, by making the shape of the radiation beam X as viewed from the emission direction approximate to the shape of the entry portion of the slit 6a of the shielding member 6, the radiation beam X that passes through the slit 6a increases while less of the radiation beam X is wastefully discarded by being blocked by the shielding units 6b. As a result, a higher dose of radiation beam X may be irradiated onto the tumor C. Moreover, the amount of electrons in the electron beam e that contribute to generating the radiation beam X passing through the slit 6a is increased by making the focal point of the radiation beam X small (in the present exemplary embodiment, the diameter of the electron beam e is shorter than the length in the length direction of the slit 6a). Thereby, a high output radiation beam can be generated without a fall in planar beam conversion efficiency, even while reducing the electron density per unit time.

In cases in which the electron beam e is swept in the y direction, generally the electron density is higher toward the center of the sweep-range of the electron beam e than at the two end sides thereof. Meanwhile, in a case in which a sine wave voltage is applied to the coil 8b the electron density at the two end sides of the sweep-range of the electron beam e is raised.

Therefore, in the radiation irradiation device 1B according to the present exemplary embodiment, sweeping of the electron beam e is performed so that the electron density becomes uniform over the electron beam e's y sweep-range by applying a triangular wave voltage to the coil 8b so that the charge amount varies according to the speed of change in emission angle of the electron beam e.

Figure 16:
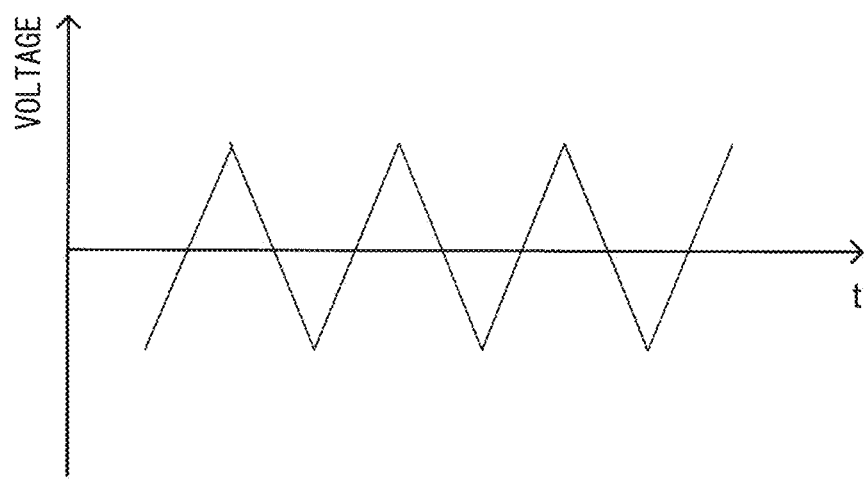
FIG. 16 is a graph illustrating an example of a voltage applied to the alternating current magnet in the radiation irradiation device according to the third exemplary embodiment.

FIG. 16 is a graph illustrating an example of a voltage applied to the alternating current magnet in the radiation irradiation device 1B according to the third exemplary embodiment. As illustrated in FIG. 16, not an ordinary sine wave but a triangular wave voltage is applied to the coil 8b of the alternating current magnet 8. Thereby an electron beam e with uniform electron density may be obtained.

Fourth Exemplary Embodiment

Detailed explanation follows regarding a radiation irradiation device 1 according to a fourth exemplary embodiment, with reference to the appended drawings. The radiation irradiation device 1 according to the fourth exemplary embodiment is configured by providing a heat transfer member 9 to the target 5 of the radiation irradiation device 1 according to the first exemplary embodiment. The same reference numerals are allocated to the same configurations as those of the first exemplary embodiment to the third exemplary embodiment, and duplicate explanation thereof is omitted.

Figure 17B:
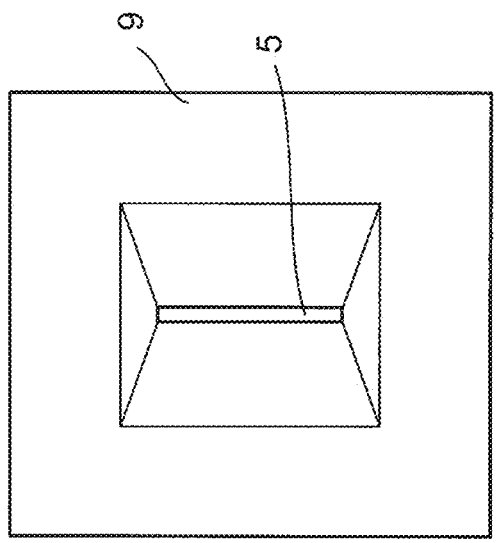
FIG. 17B is an enlarged side view illustrating a configuration of the target of the radiation irradiation device according to the fourth exemplary embodiment.
Figure 17A:
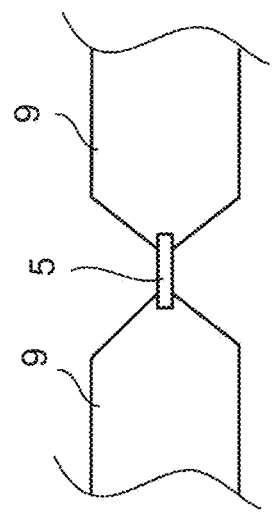
FIG. 17A is a front elevation view illustrating a configuration of a target of a radiation irradiation device according to a fourth exemplary embodiment.

FIG. 17A is a front elevation view illustrating a configuration of the target 5 of the radiation irradiation device 1 according to the fourth exemplary embodiment. FIG. 17B is an enlarged side view illustrating a configuration of the target 5 of the radiation irradiation device 1 according to the fourth exemplary embodiment.

As illustrated in FIG. 17A, the heat transfer member 9 is provided so as to surround the periphery of a region where the electron beam e is irradiated onto the target 5. The heat transfer member 9 is formed from Cu, Ag, Au, Al or the like that have high thermal conductivity. As illustrated in FIG. 17B, the heat transfer member 9 is integrally formed to the target 5 by, for example, being casted together with the target 5 so as to sandwich part of end portions of the target 5. The heat transfer member 9 also thermally coupled to the external casing (the low emittance accelerator 2b or the beam duct 2 in the present exemplary embodiment), thereby suppressing the target 5 from reaching a high temperature by absorbing heat generated in the target 5 and transferring the heat to the external casing.

In this manner, the radiation irradiation device 1 according to the fourth exemplary embodiment is capable of preventing damage to the target 5 by suppressing the target 5 from reaching a high temperature using the heat transfer member 9.

Fifth Exemplary Embodiment

Detailed explanation follows regarding a radiation irradiation device 1C according to a fifth exemplary embodiment, with reference to the appended drawings. The radiation irradiation device 1C according to the fifth exemplary embodiment is configured by providing a shielding member 6' with plural slits 6a to the radiation irradiation device 1 according to the first exemplary embodiment in place of the shielding member 6 with the single slit 6a. The same reference numerals are allocated to the same configurations as those of the first exemplary embodiment to the fourth exemplary embodiment, and duplicate explanation thereof is omitted.

Figure 18A:
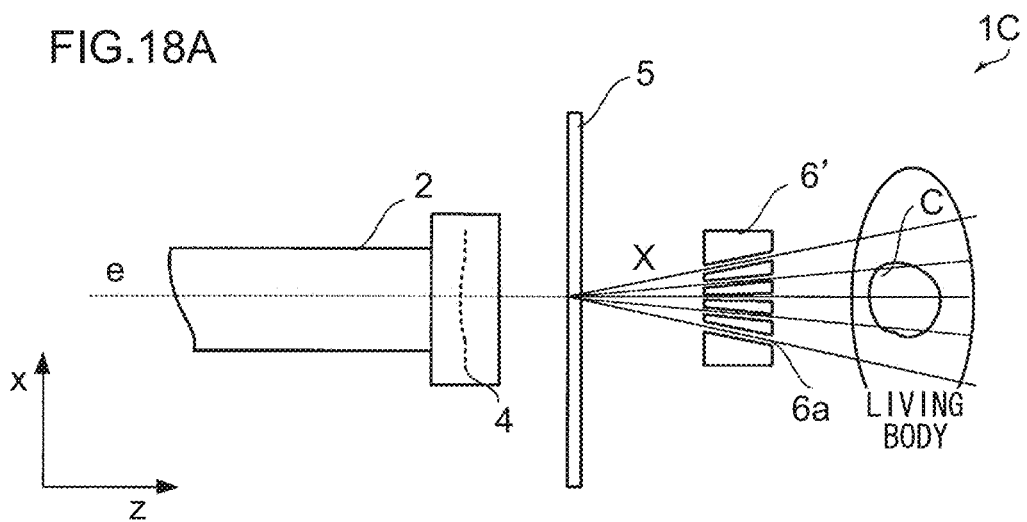
FIG. 18A is a schematic plan view illustrating relevant portions of a radiation irradiation device according to a fifth exemplary embodiment.
Figure 18B:
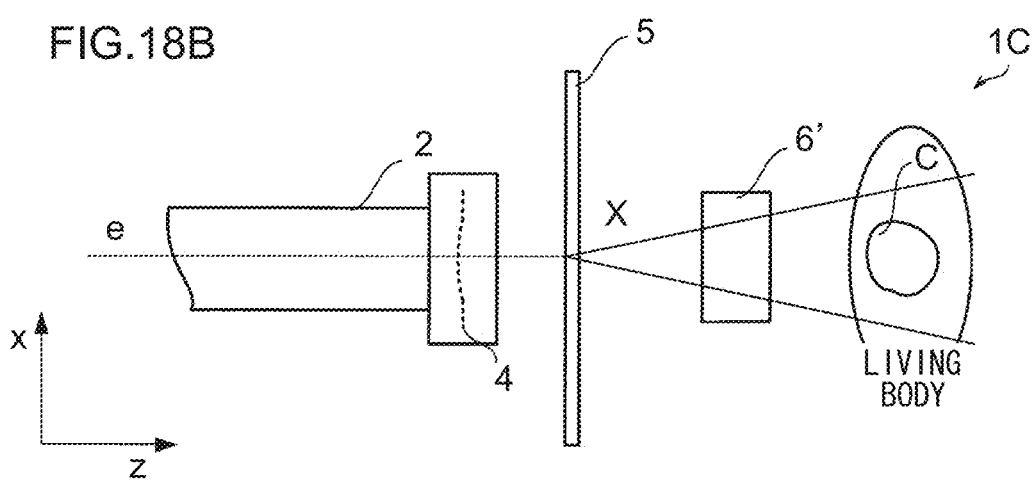
FIG. 18B is a schematic side view illustrating relevant portions of the radiation irradiation device according to the fifth exemplary embodiment.

FIG. 18A is a schematic plan view illustrating relevant portions of the radiation irradiation device 1C according to the fifth exemplary embodiment, and FIG. 18B is a schematic side view thereof. As illustrated in FIG. 18A and FIG. 18B, the radiation beam X radiated from the target 5 is incident to the shielding member 6' at the downstream side, and the radiation beam X incident to the shielding member 6' is constricted in the x direction by the plural slits 6a of the shielding member 6', and plural collimated radiation beams X that are incident to the slits 6a and pass through the shielding member 6' are irradiated onto the tumor C.

Figure 19:
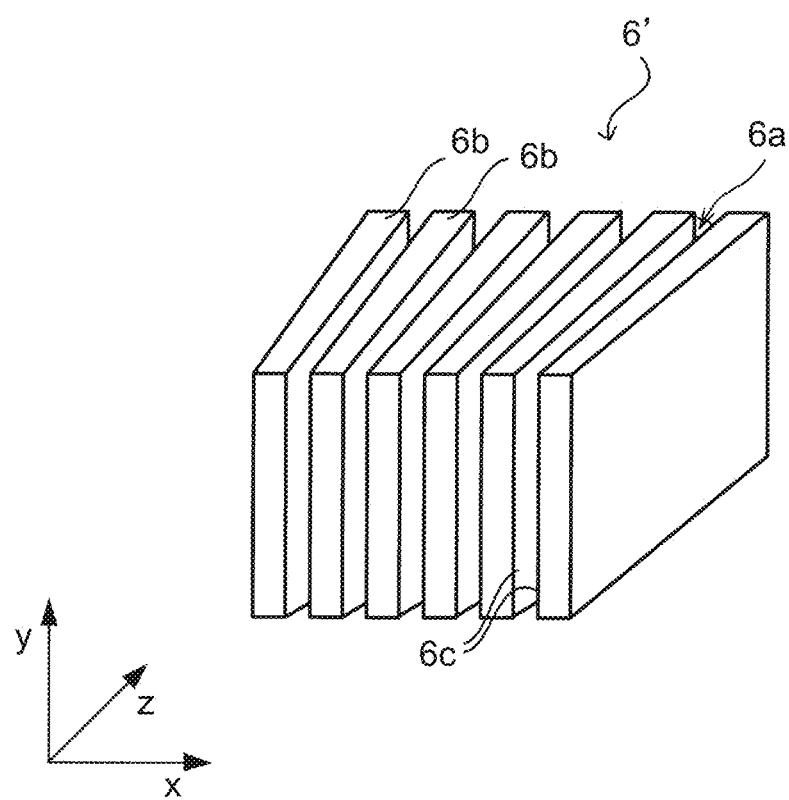
FIG. 19 is a perspective view illustrating a shielding member of the radiation irradiation device according to the fifth exemplary embodiment.

FIG. 19 is a perspective view illustrating the shielding member 6' of the radiation irradiation device 1C according to the fifth exemplary embodiment. As illustrated in FIG. 19, the shielding member 6' is configured with plural (six in the present exemplary embodiment) shielding units 6b formed from a heavy metal with excellent shielding performance to X-rays, such as W or the like. In the shielding member 6', the plural slits 6a are formed by disposing the plural shielding units 6b with gaps therebetween. Out of the radiation beam X incident to the shielding member 6', the radiation beam X incident to the slits 6a passes through the shielding member 6' and reaches behind of the shielding member 6'. However, out of the radiation beam X incident to the shielding member 6', the radiation beam X incident to the shielding units 6b is blocked by the shielding units 6b and does not reach behind of the shielding member 6'.

FIG. 20A is a schematic plan view illustrating relevant portions of the radiation irradiation device 1C according to the fifth exemplary embodiment. As illustrated in FIG. 20A, the shielding member 6' is generally formed in a sector form, with each of the slits 6a of the shielding member 6' provided at different positions so that the focal point of the radiation beam X is positioned on the extensions of the slit faces. Due to the slits 6a aligned with the radiation direction of the radiation beam X in this manner, planar beam conversion efficiency substantially equivalent to that of a parallel beam can be obtained, even though the radiation beam X spreads out in a cone shape.

Moreover, as illustrated in FIG. 19 and FIG. 20A, each of the slits 6a of the shielding member 6' is formed in the radiation beam X emission direction such that the width of the slit 6a widens (i.e., the length in the short direction becomes greater) from the entry portion where the radiation beam X is incident, to the exit portion where the radiation beams X are emitted. Thus, even if a part of the radiation beam X incident to each of the slits 6a deviates from the direction of travel at the time of incidence as it travels inside the slit 6a, there is still a high probability that the deviated X-rays are able to pass through the slit 6a, which enables as many of the X-rays to pass through the slits 6a as possible.

Although in the radiation irradiation device 1C according to the present exemplary embodiment, an example in which the plural slits 6a are gaps formed by plane portions 6c of respective adjacent shielding units 6b has been given, embodiments are not limited thereto.

In particular, a high energy radiation beam X that has high transmissivity is necessary for radiation beams used in radiation oncology treatment and, therefore, in order to generate a planar beam for MRT, there is a need of a shielding member with a thickness of about 10 cm even using a heavy metal, such as tungsten. It is extremely difficult to manufacture slits passing through this thickness with a width of 100 μm or less. Accordingly, the following manufacturing method combining plural plates may be employed.

FIG. 20B is a schematic plan view illustrating a different example of relevant portions of the radiation irradiation device 1C according to the fifth exemplary embodiment. As illustrated in FIG. 20B, the shielding member 6' may be formed by combining plural-plate-shaped shielding units 6d and plural-plate-shaped auxiliary members 6e. The auxiliary members 6e are formed from a material with a low blocking effect to X-rays. The radiation beam X incident to the regions where the auxiliary members 6e of the shielding member 6' are provided would not be blocked and reaches behind of the shielding member 6'. In this way the shielding member 6' may be manufactured more easily.

Figure 21A:
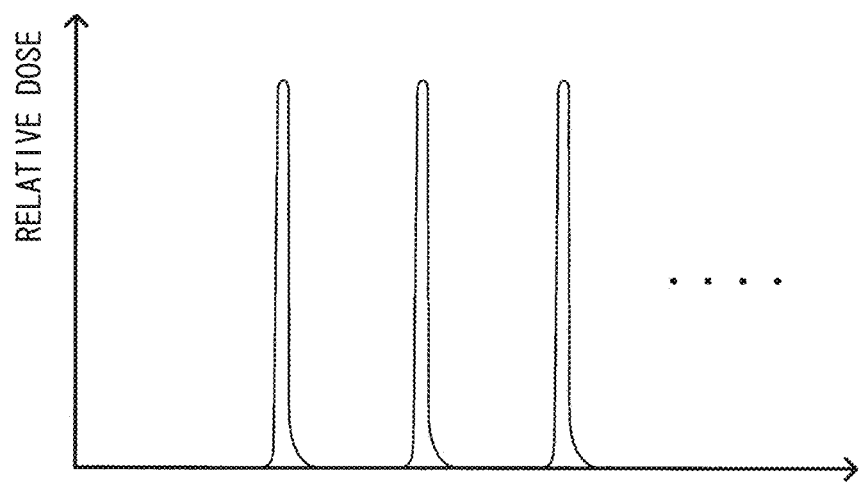
FIG. 21A is a graph illustrating a relationship between the position of a radiation beam passing through the shielding member and relative dose in the radiation irradiation device according to the fifth exemplary embodiment.
Figure 21B:
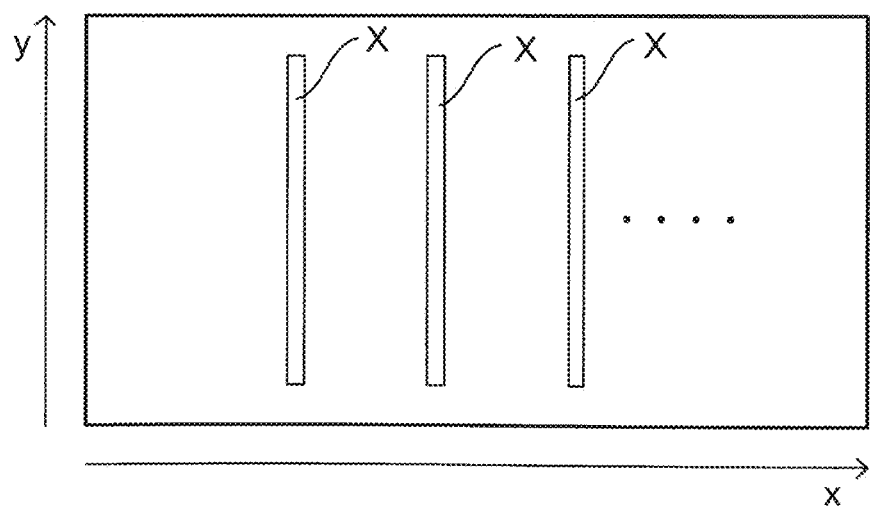
FIG. 21B is a diagram illustrating the shape of radiation beams that have passed through the shielding member of the radiation irradiation device according to the fifth exemplary embodiment, as viewed from the emission direction.

FIG. 21A is a graph that illustrates a relationship between the position of the radiation beam X passing through the shielding member 6' and the relative dose in the radiation irradiation device 1C according to the fifth exemplary embodiment. FIG. 21B is a diagram illustrating the shape of radiation beams X that have passed through the shielding member 6' of the radiation irradiation device 1C according to the fifth exemplary embodiment.

As illustrated in FIG. 21A, since out of the radiation beam X incident to the shielding member 6', only the radiation beam X that is incident to the slits 6a passes through the slits 6a, sharp peaks are generated in plural positions in the x direction where the slits 6a are provided. As illustrated in FIG. 21B, plural collimated radiation beams X that substantially match the shape of the entry portions of the slits 6a are hence formed.

Figure 22:
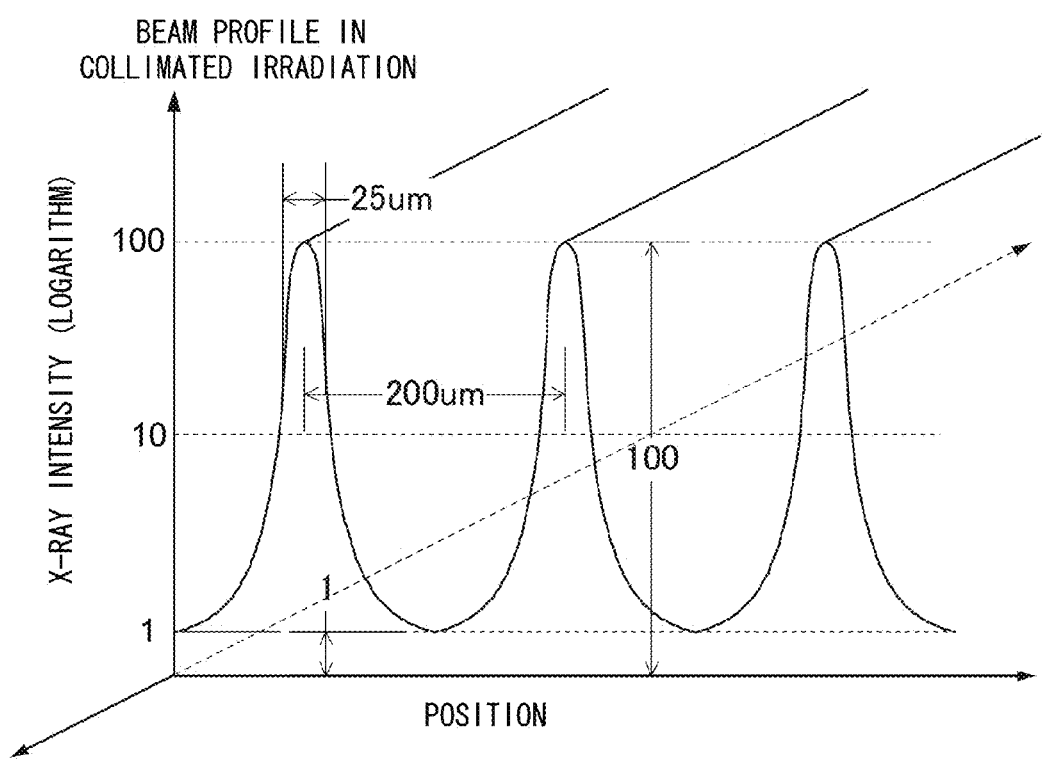
FIG. 22 is a diagram illustrating a beam profile of a radiation beam that has passed through the shielding member of the radiation irradiation device according to the fifth exemplary embodiment.

FIG. 22 is a diagram illustrating an example of a beam profile of a radiation beam X that has passed through the shielding member 6' in the radiation irradiation device 1C according to the fifth exemplary embodiment. As illustrated in FIG. 22 for example, at plural collimated radiation beams X after passing through the shielding member 6', the width of each peak is 25 μm, the pitch between respective peaks is 200 μm, and the minimum dose in the radiation beams X (the dose in regions shielded by the shielding member 6') is 1% of the peak dose.

Although the shielding units 6d of the shielding member 6' are fixed in the radiation irradiation device 1C of the present exemplary embodiment, embodiments are not limited thereto. An adjustment unit may be provided to adjust the position of each of the shielding units 6d according to the dose of the radiation beams X or the final desired shape of the radiation beams X to be generated. This enables to adjust the position of each of the slits 6a, the widths of the radiation beam entry portions for each of the slits 6a and the like.

Moreover, a configuration may be made such that the position on the target 5 of the focal point of the radiation beam X and the position of each of the shielding units 6b can be adjusted so that the focal point of the radiation beams X is positioned on the extensions of the respective slits 6a. In this way, the position of the focal point of the radiation beams X and the position of each of the slits 6a may be adjusted.

Planar radiation beams required for MRT are generated by passing a wide radiation beam through a slit in a shielding member. Multiplexing the slits has been contemplated to generate planar radiation beams with good efficiency. In this regard, since normal radiation beams spread out in a cone shape, in cases in which a multi-slit configuration in which plural slits are provided parallel to each other is used, X-rays at the center position pass through the slit, but X-rays positioned at the two end sides are unable to pass through the slits. Therefore, the advantages of the multiple slits cannot be effectively utilized.

In the radiation irradiation device 1C according to the present exemplary embodiment, the advantages of the multiple slits can be effectively utilized since the radiation beam X depth direction of each of the slits 6a is determined corresponding to the spreading cone shape of a radiation beam, and X-rays pass not only through the slit 6a positioned at the center but also the slits 6a positioned at the two end sides.

Sixth Exemplary Embodiment

Detailed explanation follows regarding a radiation irradiation device according to a sixth exemplary embodiment, with reference to the appended drawings. Note that in the radiation irradiation device according to the sixth exemplary embodiment, the radiation irradiation device 1 as explained in the first exemplary embodiment is employed, which irradiates, as a radiation beam, bremsstrahlung X-rays generated by causing an electron beam to impact onto a metal target. However, the exemplary embodiment is not limited thereto, and an radiation irradiation device that irradiates an X-ray beam generated by another method may be employed, or a radiation irradiation device that irradiates a radiation beam other than an X-ray beam may be employed.

Figure 23:
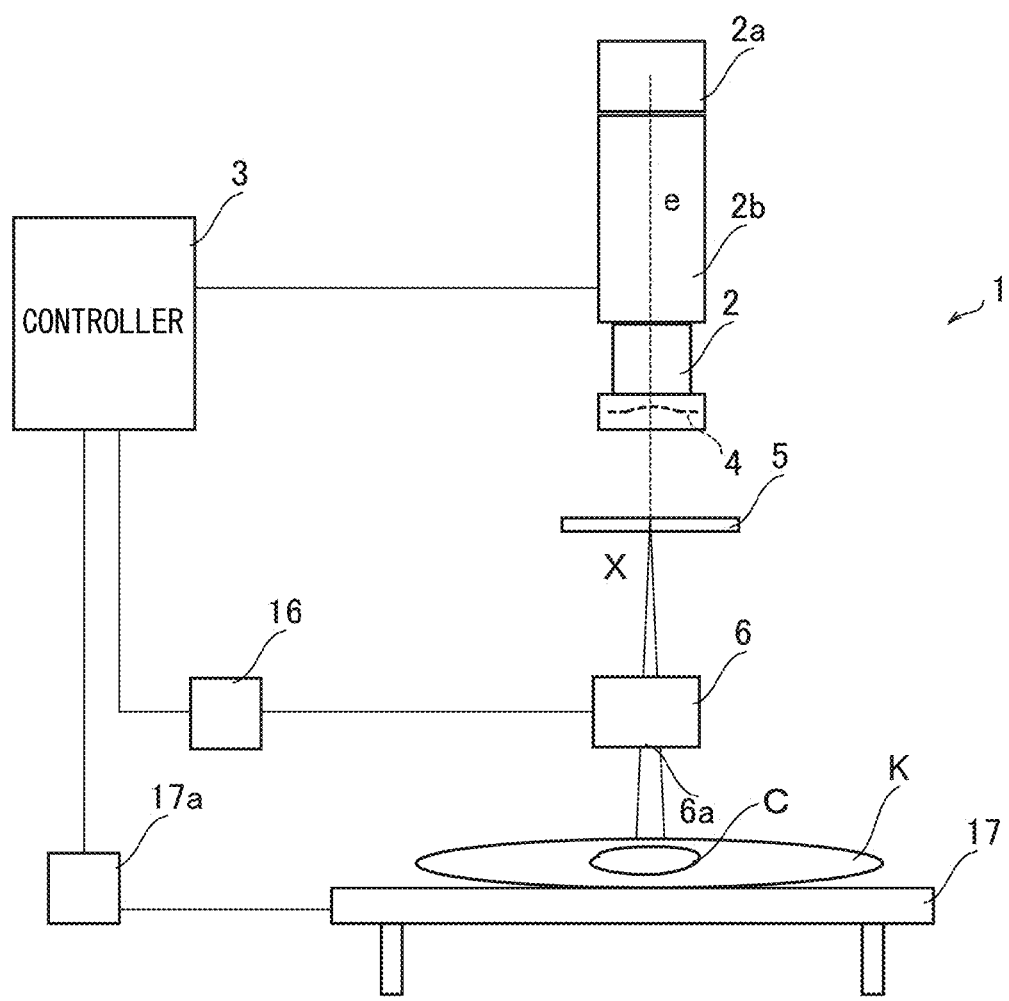
FIG. 23 is a configuration diagram illustrating an overall configuration of a radiation irradiation device according to a sixth exemplary embodiment.

FIG. 23 is a configuration diagram illustrating an overall configuration of a radiation irradiation device 1 according to the sixth exemplary embodiment. The same reference numerals are allocated to the same configurations as those of the first exemplary embodiment, and duplicate explanation thereof is omitted.

The radiation irradiation device 1 of the present invention is equipped with a controller 3 that includes a central processing unit (CPU), random access memory (RAM), and read only memory (ROM). The controller 3 effects control under the CPU of generating an electron beam e using an electron gun 2a, measuring the beam current, beam speed and beam diameter of the electron beam e accelerated by a low emittance accelerator 2b, and magnetic field adjustment using a solenoid coil according to these measurement values, as well as rotation of a shielding member 6, and movement of a bed 17, which are described later. Since the controls related to the electron gun 2a and the low emittance accelerator 2b are those currently performed in ordinary electron guns and accelerators, further explanation thereof is omitted.

The shielding member 6 with plural slits 6a that pass through a part of the radiation beam X is provided at the downstream side of a target 5 in the radiation beam X emission direction. The plural slits 6a are formed such that a width (length in the short direction) of entry portion of each of the slits 6a is smaller than the beam diameter of the radiation beam X, the width as a whole of the plural slits 6a is larger than the beam diameter of the radiation beam, and each of the slits 6a is substantially parallel to the radiation beam X emission direction.

The shielding member 6 is provided with a rotation drive device 16 mainly configured by a motor that rotationally drives the shielding member 6 around its center line in the radiation beam X emission direction, which serves as the central axis. The rotation drive device 16 is controlled by the controller 3.

For example, the shielding member 6' of the fifth exemplary embodiment illustrated in FIG. 19 may be used as the shielding member 6. As described above for the fifth exemplary embodiment, each of the plural slits 6a of the shielding member 6 is provided such that the focal point of the radiation beam X is positioned on the extensions of the slit faces, and such that each of the slit faces are facing in different directions. Providing the slits 6a in this manner corresponding to the radiation direction of the radiation beam X enables to obtain a planar beam conversion efficiency that is substantially equivalent to that of parallel beams, even though the radiation beam X spreads in a cone shape.

Although in the radiation irradiation device 1 according to the present exemplary embodiment, an example is given in which the plural slits 6a are gaps between respective adjacent shielding units 6b, embodiments are not limited thereto. The slits 6a may be formed by providing a material that has radiation transmissivity in a stripe pattern. In such cases, this material is disposed between the adjacent shielding units 6b, instead of providing the gap.

As a high energy radiation beam is required in cases using a radiation beam for human oncology treatment, in order to make the radiated radiation beam into a planar beam for use in MRT, there is a need for a shielding member with a thickness of about 10 cm (i.e., a length in the radiation beam X emission direction) even in cases using a heavy metal, such as tungsten. It is extremely difficult with current technology to manufacture slits passing through with a width (a length in the short length direction) of μm unit level in a shielding member of such a thickness. Therefore, in order to address this problem, the shielding member 6 may be formed by combining plural-plate-shaped shielding units and -plate-shaped auxiliary members. The auxiliary members are formed from a material with a low blocking effect to X-rays, such as a polyimide film. The radiation beams X that are incident to the region of the shielding member 6 where the auxiliary members are provided are not blocked, and reach behind of the shielding member 6. This enables the shielding member 6 to be manufactured relatively more easily compared to the cases in which gaps are provided in the shielding member 6.

The bed 17 (corresponding to the support member that supports the irradiation subject) on which a patient K who is receiving radiation therapy using the radiation beam X lies down, is placed at the downstream side of the shielding member 6 in the radiation beam X emission direction. The bed 17 is equipped with a movement driving device 17a, mainly configured by a motor for moving the bed 17 in a plane orthogonal to the radiation beam X emission direction. The movement driving device 17a is controlled by the controller 3. In the radiation irradiation device 1 according to the present exemplary embodiment, the movement driving device 17a is capable of moving the bed 17 in a predetermined direction orthogonal to the radiation beam X emission direction (referred to below as the x axis direction), and in a direction that is orthogonal to the radiation beam X emission direction and orthogonal to the predetermined direction (referred to below as the y axis direction).

Note that in the radiation irradiation device 1 according to the present exemplary embodiment, the radiation beam X emission direction is the direction of gravity, and the movement directions of the bed 17 are directions parallel to the floor on which the bed 17 is provided (i.e., a horizontal direction). In the radiation irradiation device 1 according to the present exemplary embodiment, MRT is performed to the whole region of the tumor C by irradiating the radiation beam X onto the tumor C of the patient K while moving the bed 17 on which the patient K lies down.

In this manner, the radiation irradiation device 1 according to the present exemplary embodiment is capable of performing radiation therapy of MRT by irradiating the radiation beam X onto the shielding member 6 that has the slits 6a, and irradiating the patient K with the planar radiation beams X that, out of the irradiated radiation beam X that has passed through the slits 6a.

FIG. 24A is a schematic plan view illustrating a manner in which the radiation beam X, generated by the electron beam e impacting the target 5, passes through the plural slits 6a of the shielding member 6 of the radiation irradiation device 1 of the sixth exemplary embodiment. FIG. 24B is a schematic side view thereof. As illustrated in FIG. 24A and FIG. 24B, due to passing through the plural slits 6a, the radiation beam X incident to the shielding member 6 is irradiated to the radiation beam X downstream side of the shielding member 6 as planar radiation beams X that extend in the y axis direction and the z axis direction.

Figure 25A:
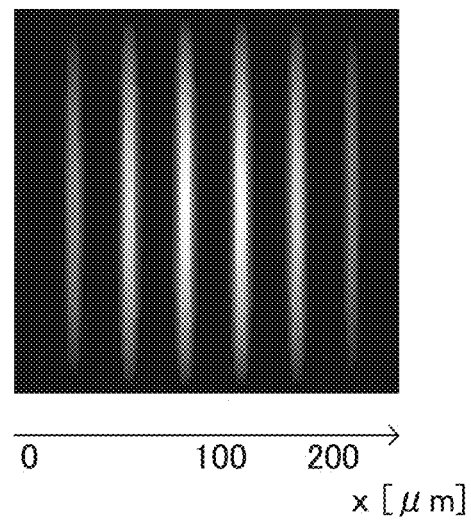
FIG. 25A is a diagram illustrating an example of a cross-section profile of radiation beams that have passed through plural slits of the shielding member of the radiation irradiation device according to the sixth exemplary embodiment, which is cut in a direction orthogonal to the direction of travel of the radiation beams.
Figure 25B:
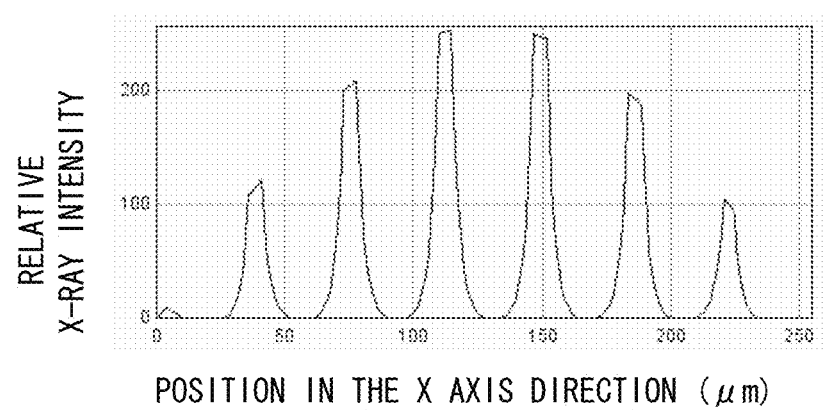
FIG. 25B is a graph illustrating a relationship between the position on the x axis direction of radiation beams that have passed through the plural slits of the shielding member and relative X-ray intensity in the radiation irradiation device according to the sixth exemplary embodiment.

FIG. 25A is an image illustrating an example of a cross-section profile of the radiation beams X that have passed through the plural slits 6a of the shielding member 6 of the radiation irradiation device 1 according to the sixth exemplary embodiment, which is cut in a direction orthogonal to the direction of travel of the radiation beams X. FIG. 25B is a graph illustrating a relationship between the position on the x axis direction of the radiation beams X that have passed through the plural slits 6a of the shielding member 6, and the relative X-ray intensity in the radiation irradiation device 1 according to the sixth exemplary embodiment.

As illustrated in FIG. 25A, out of the radiation beam X incident to the shielding member 6, only a part of the radiation beam X that is incident to the slits 6a passes through the shielding member 6, and planar radiation beams X are formed, which have cross-section profiles that substantially match the shapes of the entry portions of the slits 6a. Moreover, as illustrated in FIG. 25B, the radiation beam X incident to the shielding member 6 has sharp peaks at positions in the x axis direction where the slits 6a are provided. Moreover, as it spreads out in a cone shape, the intensity of the radiation beam X is higher at the center of the cross-section of the beam. Thus, as illustrated in FIG. 25B, the relative X-ray intensity is higher at the peak portions at the center of the cross-section view, and the relative X-ray intensity becomes lower at the peak portions toward the end sides of the cross-section view.

Figure 26:
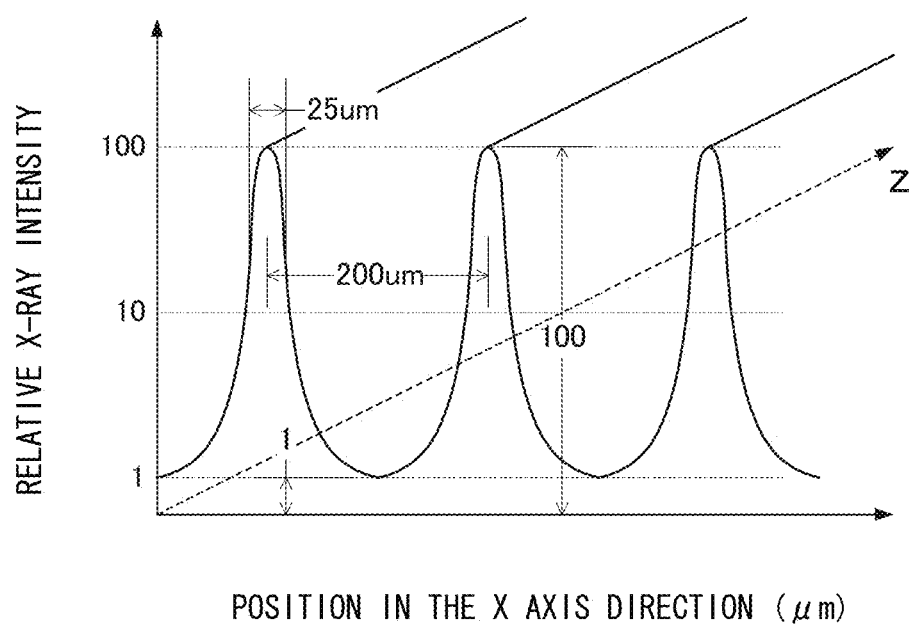
FIG. 26 is a diagram illustrating an example of a beam profile of radiation beams that have passed through the plural slits of the shielding member of the radiation irradiation device according to the sixth exemplary embodiment.

FIG. 26 is a diagram illustrating an example of a beam profile of radiation beams X that have passed through plural slits 6a of the shielding member 6 of the radiation irradiation device 1 according to the sixth exemplary embodiment. In the example illustrated in FIG. 26, after passing through the plural slits 6a of the shielding member 6, plural planar radiation beams X have a half bandwidth of 25 μm for each peak, a pitch of 200 μm between each peak, and the relative X-ray intensity at positions shielded by the shielding member 6 is 1% of the peak value of relative X-ray intensity.

During MRT, in contrast to in ordinary radiation therapy, the radiation beams used in therapy need to satisfy a predetermined condition. Specifically, the predetermined condition is that the ratio of the peak portions to the valley portions, i.e., the PV ratio, should be 10:1 or a higher ratio.

By irradiating radiation beams that satisfy this predetermined condition, it is possible to perform a radiation therapy such that the tumor cells, including those in the valley portions are destroyed due to the bystander effect (an effect that in a case of performing radiation irradiation at a low dose, cells that are not directly irradiated by the radiation are also affected), and normal cells maintain normal function, except for those destroyed in the peak portions.

In cases of generating a radiation beam used for MRT, due to limitations to the cross sectional shape of the radiation beam, it is difficult to irradiate the radiation beams X onto all of the tumor cells at once if the tumor cells are larger than the above cross sectional shape. However, it is possible to perform irradiation to all of the tumor cells by dividing the region of the irradiation target (referred to below as the "first region") and separately performing irradiation several times. In the radiation irradiation device 1 according to the present exemplary embodiment, the radiation beams X are irradiated onto the whole of the tumor C by separately performing the irradiation several times (referred to below as "divided irradiation") while moving the position of the irradiation region (referred to below as the "second region") of the radiation beams X that have passed through the slits 6a of the shielding member 6.

In cases of performing this divided irradiation, if there are gaps between each of the adjacent second regions, a therapeutic effect cannot be obtained at the gap portions since the radiation beams X are not irradiated at the gaps. Further, as described above, the radiation beams X that have passed through the plural slits 6a of the shielding member 6 have a lower X-ray intensity at peak portions toward the end sides of the cross section of the beam. In consideration of these conditions, by partly overlapping part of end portions of adjacent second regions, it is possible to reduce radiation unevenness (that is, occurrences of non-irradiated regions in the treatment target region, or occurrences of irradiation regions that do not satisfy the above conditions for MRT).

Explanation next follows regarding operation of the present exemplary embodiment.

Figure 27:
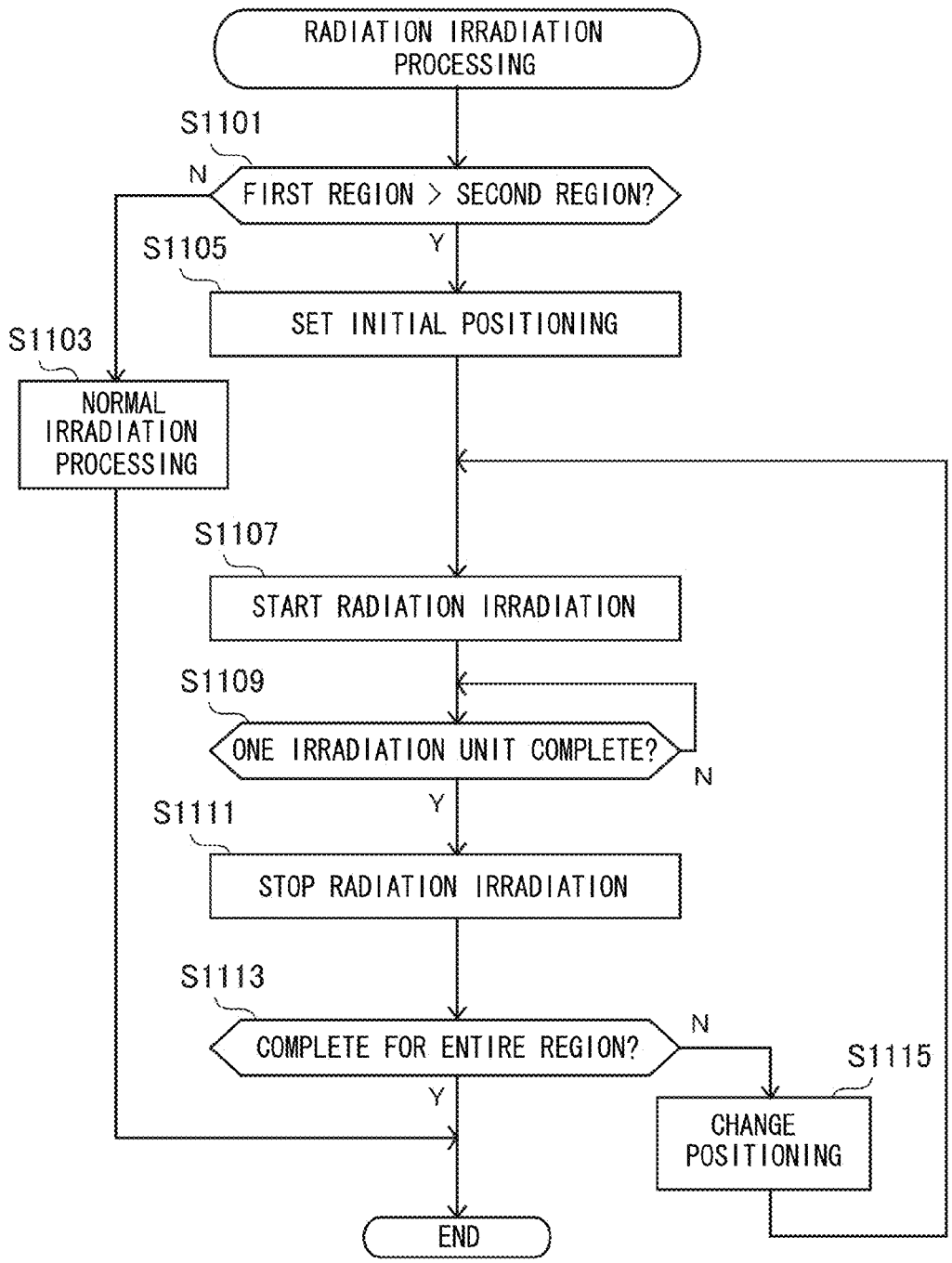
FIG. 27 is a flow chart illustrating a flow of processing in the radiation irradiation processing program according to the sixth exemplary embodiment.
Figure 28:
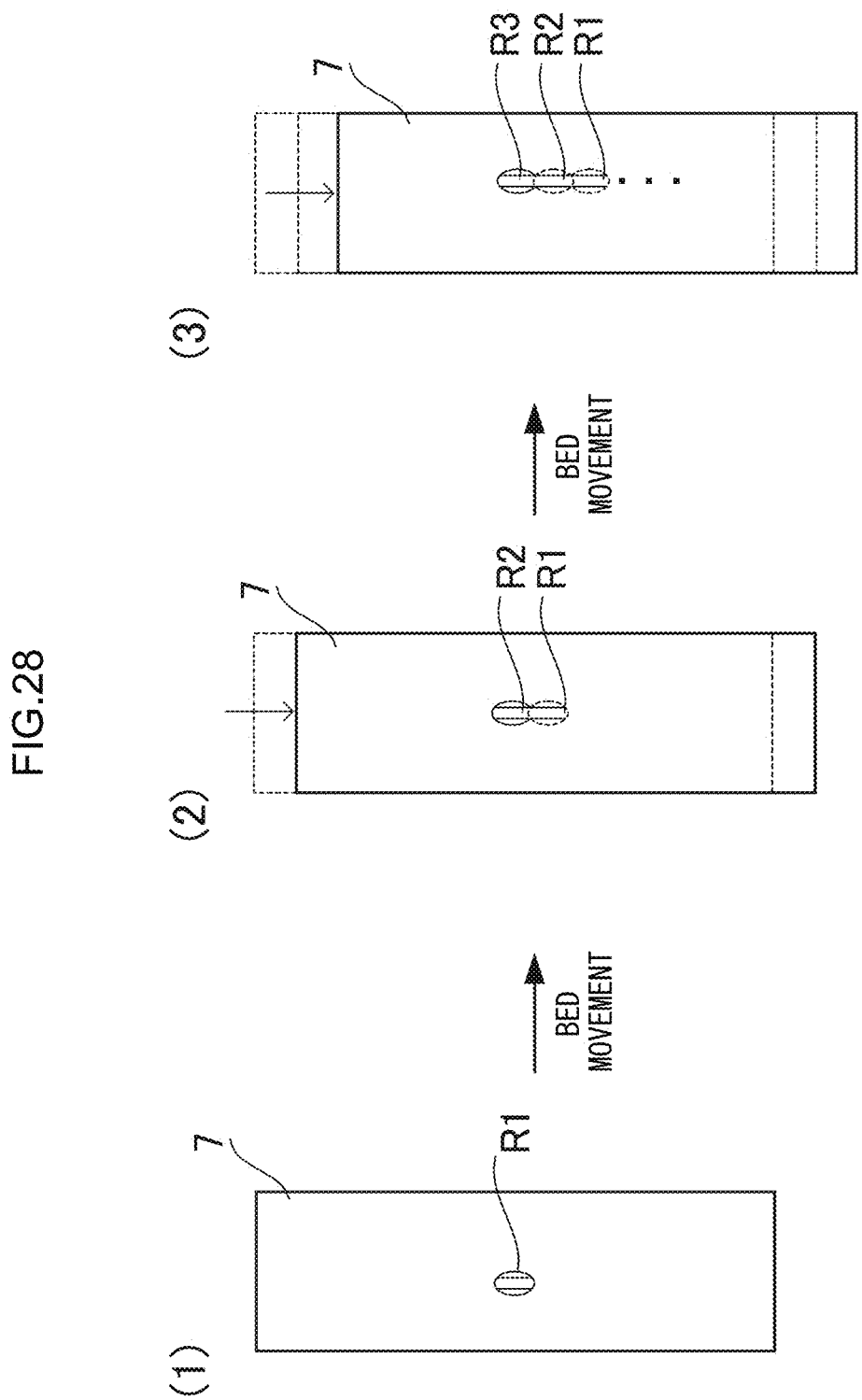
FIG. 28 is a schematic plan view for explanation of radiation irradiation processing according to the sixth exemplary embodiment.

FIG. 27 is a flow chart illustrating the flow of processing in a radiation irradiation processing program according to the first exemplary embodiment. The program is pre-stored in a specific region of the ROM that is a storage medium provided in the controller 3. FIG. 28 is a schematic plan view for explanation of the radiation irradiation processing according to the first exemplary embodiment. In FIG. 28, depiction of the patient K and the tumor C is omitted in order to facilitate understanding of the movement of the position of the second regions R1, R2, R3 . . . .

The CPU of the controller 3 executes the radiation irradiation processing program at a predetermined timing (in the present exemplary embodiment, at the timing an execution instruction is input by a user). In order to avoid complication, explanation will be given here regarding a case in which treatment is performed in a state in which the patient K lies down on the upside of the bed 17.

Prior to the execution of radiation irradiation processing, an operator of the radiation irradiation device 1, such as a radiologist or doctor, place the patient K down on the bed 17 in a position that the radiation beams X can be irradiated to the whole region of the tumor C that is the treatment target by moving the bed 17 in the movable range using the movement driving device 17a of the bed 17. The operator then inputs the controller 3 instruction data instructing execution of the radiation irradiation processing. Execution of the radiation irradiation processing program is thereby started.

After execution of the radiation irradiation processing program has been started, at step S1101, the CPU determines whether or not the first region that is the irradiation target of the radiation beams X (the entire region of the tumor C in the present exemplary embodiment) is larger than the second region. In this case, the CPU compares a plan view circumscribed rectangular frame of the tumor C that is the treatment target of the patient K as the first region and a plan view circumscribed rectangular frame of the irradiation region of the radiation beams X that have passed through the slits 6a of the shielding member 6 as the second region, and determines that the first region is smaller than the second region if the length of at least one side of the second region is longer than the corresponding side of the first region.

In a case in which it is determined at step S1101 that the first region is not larger than the second region, then at step S1103 the CPU performs normal MRT radiation irradiation to the tumor C as the treatment target of the patient K, and then ends the radiation irradiation processing.

In a case in which it is determined at step S1101 that the first region is larger than the second region, at step S1105, the CPU controls the movement driving device 17a such that the position of the bed 17 is positioned at a predetermined reference position (referred to below as the "home position") in order to perform divided irradiation. In the radiation irradiation device 1 according to the present exemplary embodiment, a position where the left-upper-corner point of the plan view circumscribed rectangular frame of the tumor C, which is the treatment target of the patient K, is included in the irradiation region of the radiation beams X by the radiation irradiation device 1, is taken as the home position. However, embodiments are not limited thereto.

At step S1107, the CPU controls the radiation irradiation device 1 so as to start MRT radiation irradiation, and then at the next step S1109, stands by until irradiation of one irradiation unit, which is predetermined according to the type and shape of the tumor C, has been completed. During this standby, as illustrated at (1) in FIG. 28, with respect to the tumor C of the patient K prone on the bed 17, the radiation beams X are irradiated to the second region R1 at the home position.

After irradiation of one irradiation unit has been completed, at the next step S1111, the CPU stops the radiation irradiation that has been started at step S1107. The method of stopping the radiation irradiation may be a method of stopping emission of radiation beam X from the electron emission window 4, or may be a method of temporarily providing a shielding member that blocks the electron beam e between the electron emission window 4 and the target 5, or temporarily providing a shielding member that blocks the radiation beams X between the target 5 and the shielding member 6 or between the shielding member 6 and the patient K.

At step S1113, the CPU determines whether or not the irradiation of the radiation beams X to the entire region of the tumor C of the patient K has been completed. In this case, the CPU determines that the irradiation to have been completed based on a completed instruction input via an input device of the controller 3. Or, the determination that the irradiation has been completed may be made by comparing the number of irradiation times pre-calculated and stored based on the shape of the second region with the number of times of irradiation at that time.

If it is determined at step S1113 that irradiation is not completed, at step S1115, the CPU controls the movement driving device 17a so as to move the position of the bed 17, and then transitions to step S1107. In this case, the CPU moves the position of the second region such that it is continuous to each of the plural divided regions divided from the first region, and such that the position of the radiation beams X that have passed through the plural slits 6a of the shielding member 6 overlap with each other in the length direction of the slits. Namely, the position of the bed 17 is moved such that the second region at previous step S1107 and the current second region partially overlap in their end portions, such that a portion of the tumor C is included in the current second region, and such that the respective planar radiation beams X in each of the second regions overlap with each other. At step S1107, the CPU again performs irradiation of the radiation beam X and thereby, as illustrated in (2) in FIG. 28, irradiates the radiation beams X such that the current second region R2 partially overlaps with the previous second region R1.

The processing of steps S1107 to S1115 is repeated until irradiation is completed at step S1113 such that, as illustrated at (3) in FIG. 28, the irradiation of the radiation beams X is performed in sequence so that each of the adjacent second regions R1, R2, R3 . . . overlap with each other.

Then, if it is determined at step S1113 that irradiation has been completed, the CPU ends execution of the radiation irradiation processing program.

Figure 29:
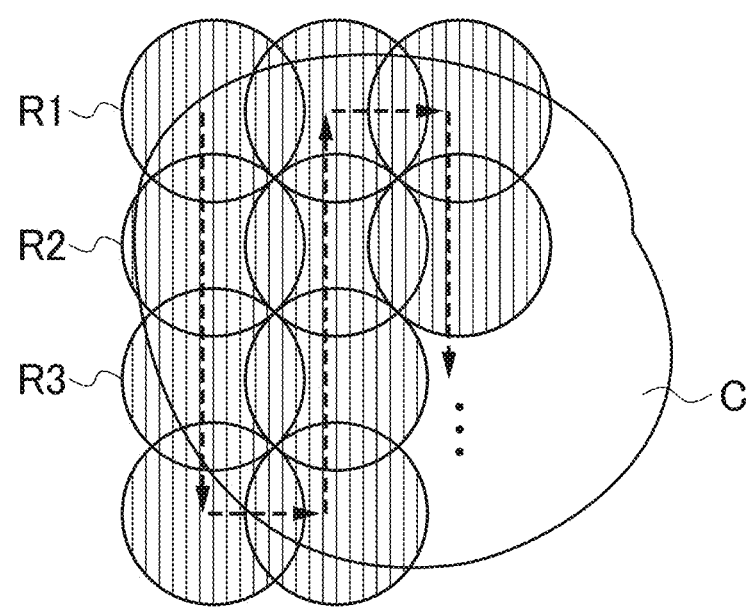
FIG. 29 is a front elevation view illustrating a manner in which a tumor is separately irradiated with radiation beams plural times in the radiation irradiation device according to the sixth exemplary embodiment.

FIG. 29 is a front elevation view illustrating a manner in which the tumor C is separately irradiated plural times with the radiation beams X. As illustrated in FIG. 29, irradiation of the radiation beams X is performed to the whole of the tumor C by separately performing irradiation plural times while shifting the position of the second regions R1, R2, R3 . . . such that portions of each of the adjacent second regions R1, R2, R3 . . . overlap with each other. The radiation beams X are also irradiated such that each of the radiation beams X that are formed in a planar shape by passing through the slit 6a overlap with each other between each of the second regions R1, R2, R3 . . . , so that the overlapped beams form a single planar radiation beam X.

Figure 30:
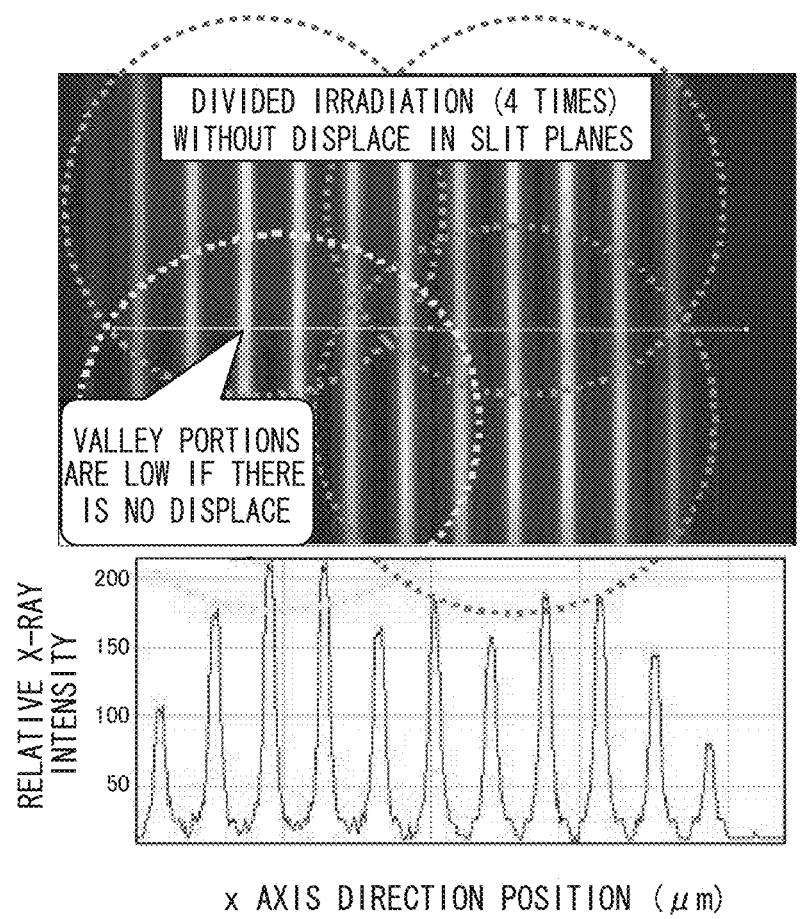
FIG. 30 is a diagram illustrating, as an example, relative X-ray intensity in an x axis direction of overlapping portions, in a case in which irradiation is separately performed plural times (by dividing an irradiation target region into two in the vertical direction and two in the horizontal direction) such that each of the positions of the planar radiation beams overlap with each other in the radiation irradiation device according to the sixth exemplary embodiment.

FIG. 30 is an image illustrating, as an example, relative X-ray intensity in the x axis direction of overlapping portions in a case in which the irradiation is separately performed plural times (by dividing the irradiation target region into two in the vertical direction and two in the horizontal direction) such that the positions of the planar radiation beams X overlap with each other. As illustrated in FIG. 30, in a region in which plural second regions are overlapped, in a case in which each of the radiation beams X formed in a planar shape by passing through the slit 6a are connected together so as to form a single planar radiation beams X, as illustrated in the graph of FIG. 30, in the region in which plural second regions are overlapped, peak portions appear at the positions corresponding to the peaks of the radiation beams X in each of the second regions, and valley portions appear at the positions between each of the adjacent peak portions.

In MRT, an excellent therapeutic effect is obtained if the relative X-ray intensity of radiation beams X is set such that an appropriate X-ray intensity is given at the peak portions while the X-ray intensity at the valley portions is kept as low as possible. Thus it is possible to obtain the excellent therapeutic effect of MRT while reducing damage to normal cells in cases of performing divided irradiation of radiation beam X by irradiating radiation beams X such that each of the radiation beams X that are formed in a planar shape by passing through the slit 6a overlap with each other between each of the second regions R1, R2, R3 . . . , and form a single planar radiation beam X.

Seventh Exemplary Embodiment

Detailed explanation follows regarding a radiation irradiation device 1 according to the seventh exemplary embodiment, with reference to the appended drawings. The radiation irradiation device 1 according to the seventh exemplary embodiment has a configuration as illustrated in FIG. 23 and FIG. 19, as the same as the radiation irradiation device 1 according to the sixth exemplary embodiment. The same reference numerals are allocated to the same configurations as those of the sixth exemplary embodiment, and duplicate explanation thereof is omitted.

Figure 31:
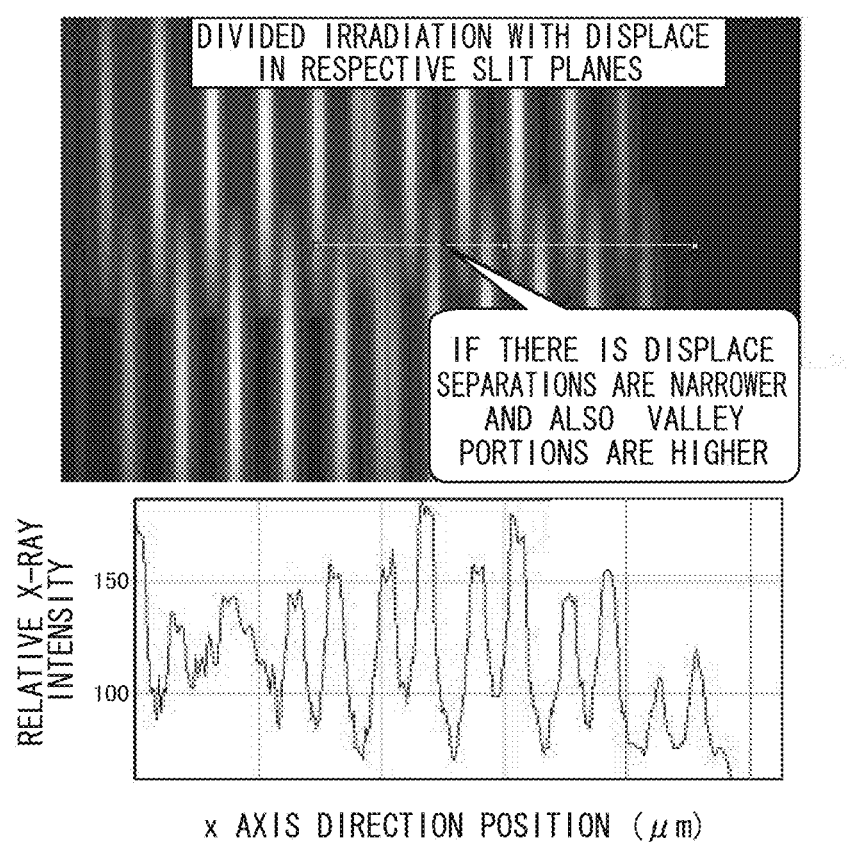
FIG. 31 is a diagram illustrating, as an example, relative X-ray intensity in the x axis direction of overlapping portions, in a case in which irradiation is separately performed plural times (by dividing the irradiation target region into four: two in the vertical direction and two in the horizontal direction) such that each of the positions of the planar radiation beams are displaced by a distance of one half the pitch between each of the slits in the radiation irradiation device according to the sixth exemplary embodiment.

FIG. 31 illustrates relative X-ray intensity in the x axis direction of overlapping portions in a case in which, for example, the irradiation is separately performed plural times (by dividing the irradiation target region into four: two in the vertical direction and two in the horizontal direction) such that the positions of the planar radiation beams X are displaced by a distance of one half the pitch between each of the slits in the radiation irradiation device according to the seventh exemplary embodiment. In cases of performing divided irradiation of radiation beam X, as illustrated in FIG. 31, if the respective radiation beams X formed in planar shapes by passing through the respective slits 6a are displaced and do not overlap with each other so that plural planar radiation beams X are generated at regions where adjacent second regions overlap with each other, there is a possibility that the relative X-ray intensity of the peak portions is lowered, and the relative X-ray intensity of the valley portions is raised, in comparison to the cases in which the planar radiation beams X overlap at the positions where the second regions overlap. As described above, it is preferable for performing MRT that the PV ratio of the radiation beams is 10:1 or a higher ratio; however, in the example illustrated in FIG. 31 it is about 3:1. Further, due to the respective planar radiation beams X not overlapping with each other between the adjacent second regions, peak portions are respectively formed by each of the planar radiation beams X in each of the second regions, resulting in a narrower separation between each of the peak portions.

Therefore, in the seventh exemplary embodiment, when moving the position of the second region for separately performing irradiation of radiation beam X plural times, the shielding member 6 is rotated by a specific angle (in the present exemplary embodiment by 90° or substantially 90°) about a rotation axis of its center line of the radiation beam X emission direction. Thereby, the direction of the radiation beams X formed in planar shapes by the radiation beam X passing through the slits 6a is changed in the adjacent second regions. Note that substantially 90° here means 90° including the mechanical allowance and tolerances of the rotation drive device 16.

Explanation next follows regarding operation of the present exemplary embodiment.

Figure 32:
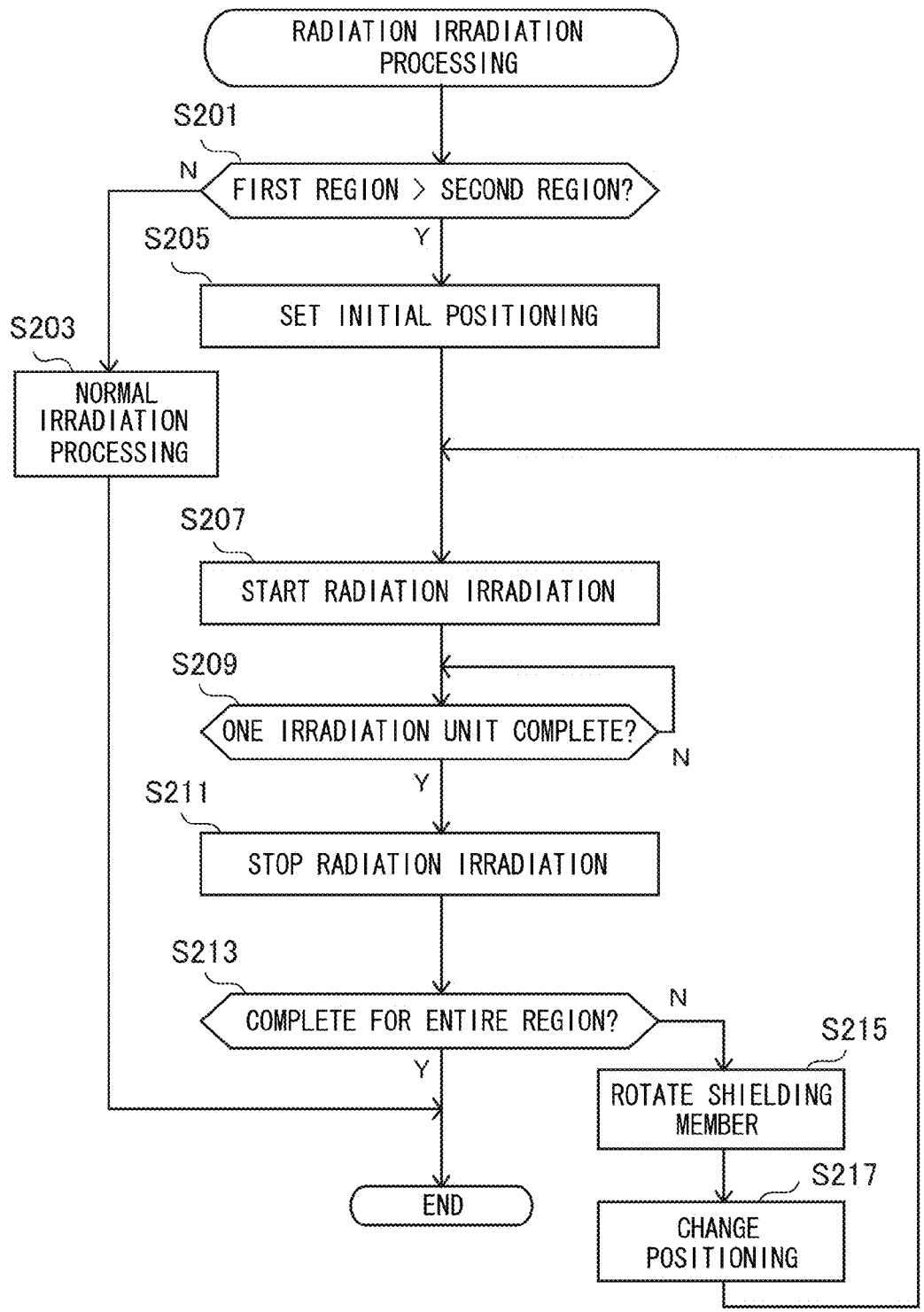
FIG. 32 is a flow chart illustrating a flow of processing in a radiation irradiation processing program according to a seventh exemplary embodiment.
Figure 33:
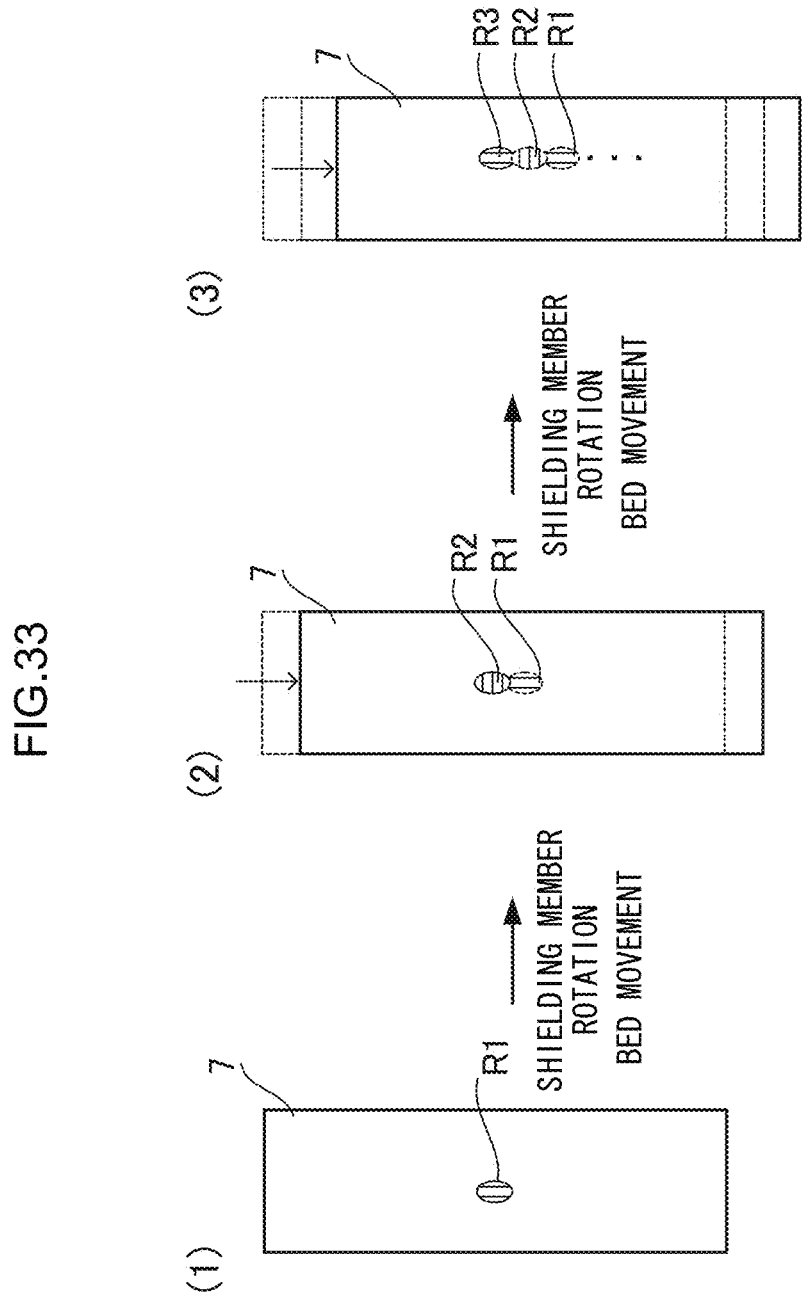
FIG. 33 is a schematic plan view for explanation of radiation irradiation processing according to the seventh exemplary embodiment.

FIG. 32 is a flow chart illustrating a flow of processing in a radiation irradiation processing program according to the seventh exemplary embodiment. The program is pre-stored in a specific region of the ROM that is a storage medium provided in the controller 3. FIG. 33 is a schematic plan view for explanation of the radiation irradiation processing according to the seventh exemplary embodiment. In FIG. 33, depiction of the patient K and the tumor C is omitted in order to facilitate understanding of the movement of the position of the second region.

The CPU of the controller 3 executes the radiation irradiation processing program at a predetermined timing (in the present exemplary embodiment, at the timing an execution instruction is input by a user). Similarly to in the sixth exemplary embodiment, explanation follows regarding a case in which treatment is performed in a state in which the patient K lies down on the upside of the bed 17.

At steps S201 to S209, the CPU performs processing similar to as that of steps S1101 to S1109 of the sixth exemplary embodiment. While the standby at step S209, as illustrated at (1) in FIG. 33, the radiation beams X are irradiated onto the second region R1 at the home position with respect to the tumor C of the patient K lying on the bed 17.

Then, the CPU performs processing at steps S211 and S213, which is similar to as the processing at step S1111 and S1113 of the sixth exemplary embodiment.

If it is determined at step S213 that irradiation has not been completed, then at step S215 the CPU controls the rotation drive device 16 so as to rotate the shielding member 6 about its center line along the emission direction of the radiation beams X, which serves as a rotation axis. In this case, the CPU controls the rotation drive device 16 so as to rotate the shielding member 6 such that the planar radiation beams X in the previous second region, and the planar radiation beams X in the current second region are angled at substantially 90° to each other.

In step S217, the CPU controls the movement driving device 17a so as to move the position of the bed 17 and then transitions to step S207. In this case, the CPU moves the position of the second region to be continuous with each of the divided regions formed by dividing the first region into plural regions. Namely, the CPU moves the bed 17 such that the end portions of the second region of previous step S207 and the current second region partially overlap with each other, and also such that a portion of the tumor C is included in the current second region. At step S207, by the CPU again performing irradiation of radiation beam X, as illustrated at (2) in FIG. 33, irradiation of radiation beam X is performed such that a portion of the current second region R2 and the previous second region R1 overlap with each other, and the planar radiation beams X in the second region R1 and the planar radiation beams X in the second region R2 form an angle of 90°.

The processing of step S207 to step S217 is repeated until irradiation is completed at step S213. Thereby, as illustrated at (3) of FIG. 33, irradiation of the radiation beams X is performed in sequence such that mutually adjacent second regions R1, R2, R3 . . . overlap with each other, and also the planar radiation beams X for adjacent second regions are at an angle of 90°.

If it is determined at step S213 that the irradiation has been completed, the CPU ends the execution of the radiation irradiation processing program.

Figure 34:
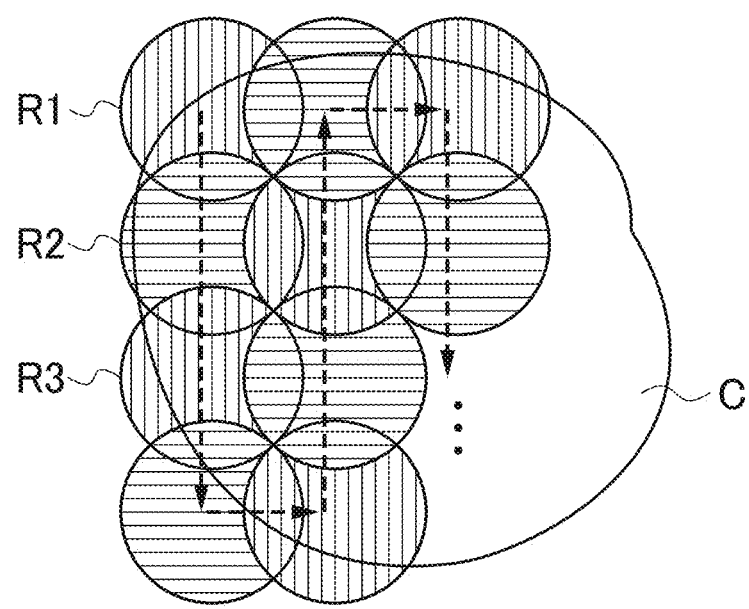
FIG. 34 is a diagram illustrating a manner in which a tumor is separately irradiated with the radiation beams plural times in the radiation irradiation device according to the seventh exemplary embodiment.

FIG. 34 illustrates a manner in which the tumor C is separately irradiated with the radiation beams X plural times. As illustrated in FIG. 34, irradiation of the radiation beams X is performed to the whole of the tumor C by separately irradiating radiation beams X plural times while shifting the position of the second regions R1, R2, R3 . . . such that a portion of each of the second regions R1, R2, R3 . . . overlap with each other, and while rotating the shielding member 6 about its center line in the radiation beams X emission direction as a rotation axis, such that the radiation beams X for adjacent second regions R1, R2, R3 . . . , which are formed in planar shapes by passing through plural slits 6a of the shielding member 6, are irradiated with an angle at 90° to each other.

Figure 35:
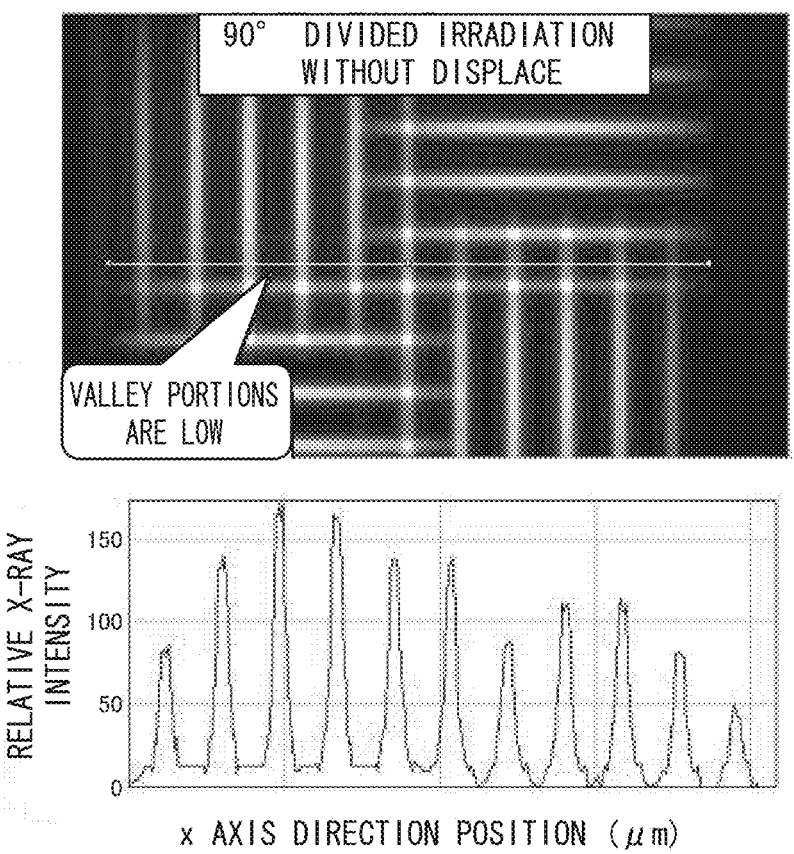
FIG. 35 is a diagram illustrating, as an example, relative X-ray intensity in the x axis direction of overlapping portions, in a case in which irradiation is separately performed plural times (by dividing the irradiation target region into four: two in the vertical direction and two in the horizontal direction) such that each of the positions of the planar radiation beams overlap with each other in the radiation irradiation device according to the seventh exemplary embodiment.

FIG. 35 is an image illustrating relative X-ray intensity in the x axis direction of the overlapping portions in a case in which, for example, the irradiation is separately performed plural times (by dividing the irradiation target region into four: two in the vertical direction and two in the horizontal direction) such that the positions of the planar radiation beams X overlap with each other. As illustrated in FIG. 35, in cases in which irradiation is performed such that the respective planar radiation beams X in regions where plural second regions overlap with each other join together in each of the second regions to form a single planar radiation beam X, as illustrated in the graph of FIG. 35, at the positions where the plural second regions are overlapped, peaks in relative X-ray intensity are shown at the positions corresponding to the peaks of the radiation beams X in each of the second regions.

In the divided irradiation of the radiation beams X, an excellent therapeutic effects of MRT can be obtained by adjusting the position of the second region of the radiation beams X and performing irradiation such that the respective planar radiation beams X in each of the second regions join together and form a single planar radiation beam X in the regions where the plural second regions overlap with each other.

Figure 36:
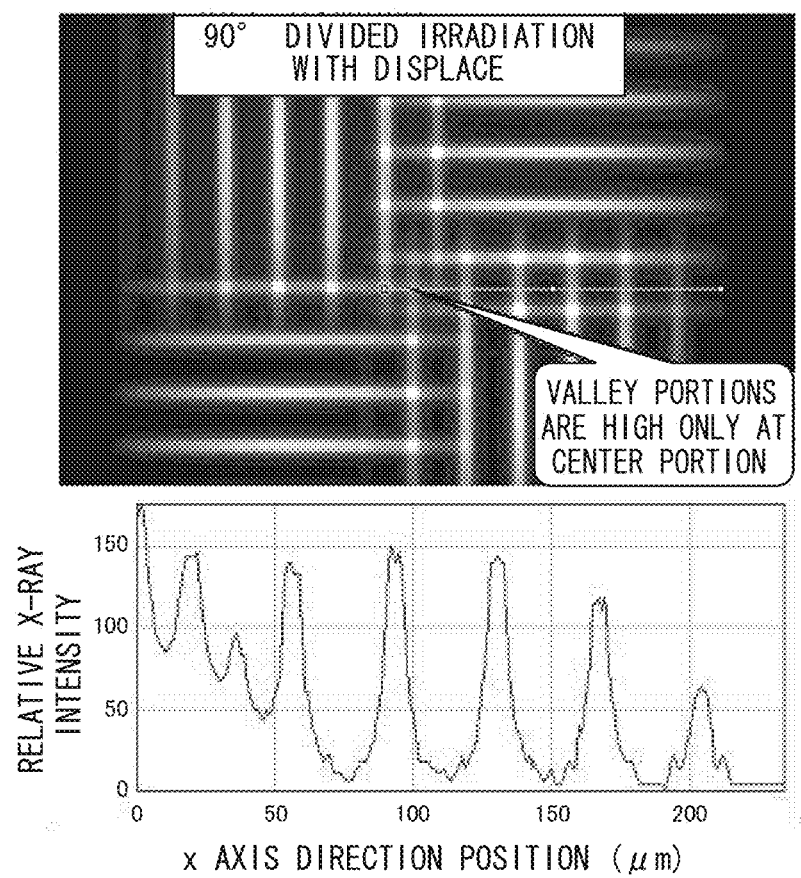
FIG. 36 is a diagram illustrating, as an example, relative X-ray intensity in the x axis direction of overlapping portions, in a case in which irradiation is separately performed plural times (by dividing the irradiation target region into four: two in the vertical direction and two in the horizontal direction) such that the positions of the planar radiation beams are displaced by a distance of one half the pitch between each of the slits in the radiation irradiation device according to the seventh exemplary embodiment.

Moreover, FIG. 36 is an image illustrating relative X-ray intensity in the x axis direction of overlapping portions in a case in which, for example, the irradiation is separately performed plural times (by dividing the irradiation target region into four: two in the vertical direction and two in the horizontal direction) such that the positions of the planar radiation beams X are displaced by a distance of one half the pitch between each of the slits. In the divided irradiation of the radiation beams X, as illustrated in FIG. 36, even in cases in which the positions of the planar radiation beams X in each of the second regions are displaced and does not overlap with each other at the region where the plural second regions overlap with each other, it is possible to secure the relative X-ray intensities of the peak portions at the region where the plural second regions overlap with each other to be a specific value or greater, and also to suppress the relative X-ray intensity of the valley portions to a specific value or lower.

In the sixth exemplary embodiment and the seventh exemplary embodiment, since the irradiation of the tumor C is performed with the radiation beam X that has been generated by causing the electron beam e to impact onto the target 5 and that has directly passed through the plural slits 6a of the shielding member 6, the cross-section profile of the second regions cut in a plane orthogonal to the emission direction of the radiation beams X is a circular shape. However, embodiments are not limited thereto.

Figure 37A:
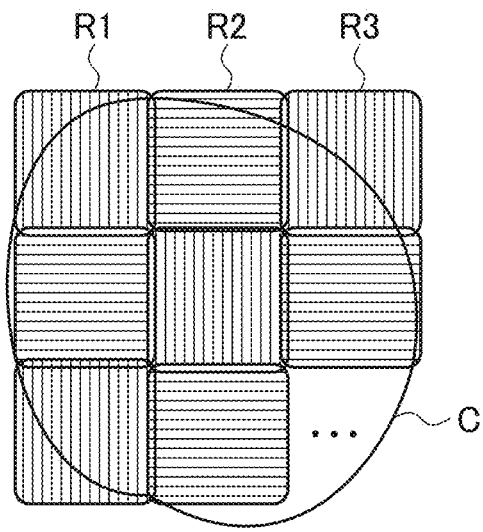
FIG. 37A is a front elevation view illustrating irradiation of radiation beams X onto a tumor at the radiation irradiation device according to another exemplary embodiment.
Figure 37B:
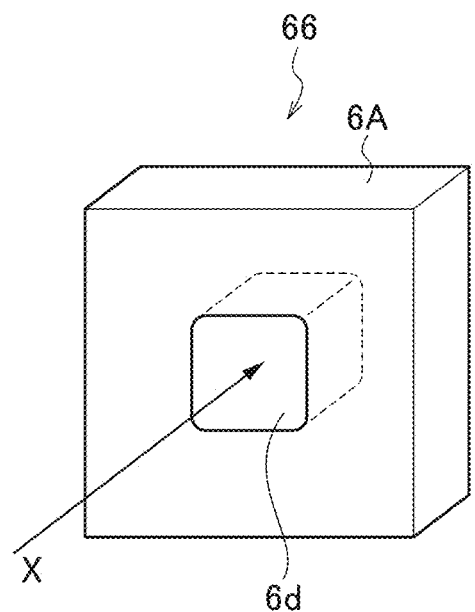
FIG. 37B is a perspective view illustrating an example of the external appearance of a shielding member used in another exemplary embodiment.

FIG. 37A is a plan view of another example of irradiation of radiation beams X onto the tumor C applied to the sixth exemplary embodiment and the seventh exemplary embodiment. FIG. 37B is a perspective view illustrating an example of the external appearance of a shielding member employed in this another example. FIG. 37A and FIG. 37B depict a case in which the embodiment of another example is applied to the seventh exemplary embodiment. The profile of the second regions may be formed in a rectangular shape, as illustrated in FIG. 37A. In such cases, a shielding member 66 illustrated in FIG. 37B is provided as a separate component to the shielding member 6, and is disposed at the upstream side or the downstream side of the shielding member 6 in the radiation beam X emission direction. The shielding member 66 is has a rectangular shaped radiation passing portion 6d though which a radiation beam X passes. The radiation beam X incident to the shielding member 66 is collimated into a rectangular shaped cross-sectional profile and emitted from the shielding member 66.

Embodiments are not limited to the configuration in which the shielding member 66 is provided as a separate component to the shielding member 6. By providing plural slits 6a only in a rectangular shaped region of the shielding member 6, the radiation beam X incident to the shielding member 6 may be collimated into a rectangular shape and then formed into planar radiation beams X by plural slits 6a. In such cases, by only passing through the radiation beam X that is incident to the plural slits 6a and also incident to the predetermined rectangular shape region pass through, the cross-sectional profile of the radiation beams X irradiated onto the patient K in a plane orthogonal to the emission direction becomes a rectangular shape, thereby enabling the radiation beams X to be irradiated onto the plural second regions without separations while making the overlapping regions of the plural second regions small.

Further, in the sixth exemplary embodiment and the seventh exemplary embodiment, the radiation beams X are rotated by rotating the shielding member 6 about a rotation axis of its center line in the radiation beams X emission direction. However, embodiments are not limited thereto, and the rotation may be performed together with movement of the bed 17.

Further, although in the second exemplary embodiment and the seventh exemplary embodiment, the position of the second region is moved by moving the bed 17, embodiments are not limited thereto. The position of the second region may be moved by changing the emission position and/or emission direction of the electron beam e emitted from the electron emission window 4. Alternatively, the position of the second region may be moved by changing the position and/or angle of the plural slits 6a in the shielding member 6.

Moreover, in the sixth exemplary embodiment and the seventh exemplary embodiment, the bremsstrahlung X-rays are generated by causing the electron beam e to impact onto the target 5, and these bremsstrahlung X-rays are used as radiation beams X for MRT. However, embodiments are not limited thereto, and the synchrotron radiation described above or gamma rays may be used.

What is claimed is:

1. A radiation irradiation device, comprising:
a metal target that emits bremsstrahlung X-rays as a radiation beam due to irradiation with an electron beam, the radiation beam emitted from the metal target spreading out in a cone shape;
a radiation shielding member that includes a plurality of slit-shaped radiation passage portions and that is disposed downstream of the metal target in the radiation beam emission direction and is disposed such that a portion of the radiation beam passes through the radiation passage portions and the radiation beam incident to regions other than the radiation passage portions is blocked;
an electron beam generating device that irradiates, onto the metal target, an electron beam such that a diameter at a generation point of the emitted radiation beam is smaller than a length of an entry portion of the radiation passage portion along a length direction of the entry portion; and
a control unit that effects control of moving at least one of a first region or a second region, the first region being an irradiation target of the radiation beam and the second region being an irradiation region of the radiation beam that has passed through the radiation shielding member, the moving being performed by relatively moving the second region with respect to the first region such that the radiation beam that has passed through the radiation passage portions partially overlaps before and after the moving, wherein the plurality of radiation passage portions are disposed at different positions such that the generation point of the radiation beam is positioned at an intersection point of slit planes of the radiation passage portions.

2. The radiation irradiation device of claim 1, further comprising a control unit that effects control of forming the electron beam emitted by the electron beam generating device in an elongated shape that is elongated along the length direction of the entry portion of the radiation passage portion, at a stage prior to irradiation onto the metal target.

3. The radiation irradiation device of claim 1, further comprising a control unit that effects control of moving an irradiation position of the electron beam emitted from the electron beam generating device onto the metal target along a direction corresponding to the length direction of the entry portion of the radiation passage portion.

4. The radiation irradiation device of claim 3, wherein the control unit effects control of moving the irradiation position of the electron beam onto the metal target by changing an emission angle of the electron beam emitted from the electron beam generating device.

5. The radiation irradiation device of claim 4, wherein the control unit effects control of changing an electrical charge amount of the electron beam according to a speed of change during the changing of the emission angle of the electron beam.

6. The radiation irradiation device of claim 1, wherein the metal target is formed so as to have a minimum thickness such that the metal target is not damaged by the electron beam when irradiated with the electron beam.

7. The radiation irradiation device of claim 1, further comprising a heat transfer member that is thermally coupled to a casing of the electron beam generating device or to an external casing, and is provided so as to contact at least a portion of the metal target.

8. The radiation irradiation device of claim 7, wherein the heat transfer member is provided so as to surround a region of the metal target that is irradiated with the electron beam.

9. The radiation irradiation device of claim 1, wherein a width of the entry portion of the radiation passage portion is from 20 μm to 1 mm.

10. The radiation irradiation device of claim 1, wherein a dose of the electron beam is determined such that a dose of the radiation beam that has passed through the radiation passage portion is from 1 Gy to 1000 Gy, and a dose of the radiation beam that has not been blocked and has passed through a region of the radiation shielding member other than at the radiation passage portion is from $1/1000^{th}$ to $1/10^{th}$ part of the dose of the radiation beam that has passed through the radiation passage portion.

11. The radiation irradiation device of claim 1, wherein the radiation shielding member is formed by combining a plurality of plate-shaped shielding members.

12. The radiation irradiation device of claim 1, wherein each of the plurality of radiation passage portions is formed so as to gradually widen from the entry portion at which the radiation beam is incident toward an exit portion at which the radiation beam is emitted.

13. The radiation irradiation device of claim 1, further comprising an adjustment unit that adjusts a width of the entry portion of each of the plurality of radiation passage portions.

14. The radiation irradiation device of claim 1, further comprising an adjustment unit that adjusts mutual positional relationships between the generation point of the radiation beam and the plurality of radiation passage portions of the radiation shielding member.

15. The radiation irradiation device of claim 1, wherein the radiation shielding member is configured by arraying a plurality of shielding members that are respectively equipped with a face that forms the radiation passage portion between the face and a corresponding face of an adjacent shielding member, such that the generation point of the radiation beam is positioned at extensions in the depth direction of each of the formed radiation passage portions.

16. The radiation irradiation device of claim 1, wherein the control unit effects control during the control of the movement, such that the radiation beam that has passed through the slit-shaped radiation passage portion partially overlaps before and after the moving in the length direction of the slit-shaped radiation passage portion.

17. The radiation irradiation device of claim 1, wherein the control unit effects control during the control of the movement, such that the second region after the moving is rotated about the emission direction of the radiation beam by 90° from before the moving.

18. The radiation irradiation device of claim 17, wherein the control unit effects control of rotating the second region by rotating the radiation shielding member.

19. The radiation irradiation device of claim 1, wherein the control unit effects control of moving the second region by moving a support member that supports a subject of irradiation by the radiation beam.

20. The radiation irradiation device of claim 1, wherein the radiation shielding member is formed such that the second region is a rectangular shaped region.

21. The radiation irradiation device of claim 1, further comprising:
a determination unit that determines whether or not the first region is larger than the second region; and
if it is determined by the determination unit that the first region is larger than the second region, the control unit effects control of the movement such that the first region is divided into a plurality of regions each having a size corresponding to the second region, adjacent regions of the plurality of regions overlap with each other, and each of the divided regions is taken as the second region.

* * * * *